(12) United States Patent
Kitagawa

(10) Patent No.: US 7,276,381 B2
(45) Date of Patent: Oct. 2, 2007

(54) MONOMERS AND POLYMERS HAVING ENERGY ABSORBING MOIETIES OF USE IN DESORPTION/IONIZATION OF ANALYTES

(75) Inventor: Naotaka Kitagawa, Fremont, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 326 days.

(21) Appl. No.: 10/326,219

(22) Filed: Dec. 20, 2002

(65) Prior Publication Data

US 2003/0207460 A1 Nov. 6, 2003

Related U.S. Application Data

(63) Continuation-in-part of application No. 10/327,511, filed on Dec. 19, 2002.

(60) Provisional application No. 60/408,255, filed on Sep. 4, 2002, provisional application No. 60/351,971, filed on Jan. 25, 2002.

(51) Int. Cl.
*G01N 24/00* (2006.01)
(52) U.S. Cl. .................. 436/173; 436/155; 436/178
(58) Field of Classification Search .................. None
See application file for complete search history.

(56) References Cited

U.S. PATENT DOCUMENTS

| | | | |
|---|---|---|---|
| 3,070,442 A | 12/1962 | Cohen et al. | |
| 4,551,420 A * | 11/1985 | Sugimoto et al. | ........... 430/505 |
| 5,002,582 A | 3/1991 | Guire et al. | |
| 5,719,060 A | 2/1998 | Hutchens et al. | |
| 5,741,551 A | 4/1998 | Guire et al. | |
| 5,770,860 A * | 6/1998 | Franzen | ........... 250/288 |
| 5,894,063 A * | 4/1999 | Hutchens et al. | ........... 436/155 |

FOREIGN PATENT DOCUMENTS

| | | |
|---|---|---|
| JP | 04-071896 A | 3/1992 |
| JP | 11165052 A | 6/1999 |
| WO | WO 96/41842 | 12/1996 |

OTHER PUBLICATIONS

Voivodov et al. "Surface arrays of energy absorbing polymers enabling covalent attachment of biomolecules for subsequent laser-induced uncoupling/desorption", Tetrahedron Lett., 1996, v. 37, No. 32, pp. 5669-5672.*

Hutches et al. "New desorption strategies for the mass spectrometric analysis of macromolecules", Rapid Commun. Mass Spectrom., 1993, v. 7, pp. 576-580.*

* cited by examiner

*Primary Examiner*—Yelena G. Gakh
(74) *Attorney, Agent, or Firm*—Morgan, Lewis & Bockius LLP

(57) ABSTRACT

The present invention provides polymerizable monomers that incorporate moieties derived from energy absorbing molecules (EAM). The invention also provides polymers that are based on the monomers. The polymers have unique properties that make them ideally suited for use in diverse analyses, including desorption/ionization mass spectrometry of analytes. The invention also provides a device that incorporates the polymeric compositions of the inventions, methods of using the device to detect, quantify and identify analytes, and a method of preparing a device of the invention.

26 Claims, 16 Drawing Sheets

MONOMERS AND POLYMERS HAVING ENERGY ABSORBING MOIETIES OF USE IN DESORPTION/IONIZATION OF ANALYTES

CROSS-REFERENCE TO RELATED APPLICATIONS

This application claims the benefit of U.S. patent application Ser. No. 10/327,511 filed Dec. 19, 2002, which claims the benefit of provisional patent application No. 60/351,971, filed Jan. 25, 2002 and U.S. provisional patent application No. 60/408,255, filed Sep. 4, 2002, the disclosure of each of which is incorporated herein by reference in its entirety for all purposes.

BACKGROUND OF THE INVENTION

Bioassays are used to probe for the presence and/or the quantity of an analyte material in a biological sample. In surface based assays, the analyte is quantified by its capture and detection on a solid support. One example of a surface-based assay is a DNA microarray. The use of DNA microarrays has become widely adopted in the study of gene expression and genotyping due to the ability to monitor large numbers of genes simultaneously (Schena et al., Science 270:467-470 (1995); Pollack et al., Nat. Genet. 23:41-46 (1999)). More than 100,000 different probe sequences can be bound to distinct spatial locations across the microarray surface, each spot corresponding to a single gene (Schena et al., Tibtech 16:301-306 (1998)). When a fluorescent-labeled DNA analyte sample is placed over the surface of the array, individual DNA strands hybridize to complementary strands within each array spot. The level of fluorescence detected quantifies the number of copies bound to the array surface and therefore the relative presence of each gene, while the location of each spot determines the gene identity. Using arrays, it is theoretically possible to simultaneously monitor the expression of all genes in the human genome. This is an extremely powerful technique, with applications spanning all areas of genetics. (For some examples, see the Chipping Forecast supplement to Nature Genetics 21 (1999)). Arrays can also be fabricated using other binding moieties such as antibodies, proteins, haptens or aptamers, in order to facilitate a wide variety of bioassays in array format.

Other surface-based assays include microtitre plate-based ELISAs in which the bottom of each well is coated with a different antibody. A protein sample is then added to each well along with a fluorescent-labeled secondary antibody for each protein. Analyte proteins are captured on the surface of each well and secondarily labeled with a fluorophore. The fluorescence intensity at the bottom of each well is used to quantify the amount of each analyte molecule in the sample. Similarly, antibodies or DNA can be bound to a microsphere such as a polymer bead and assayed as described above. Once again, each of these assay formats is amenable for use with a plurality of binding moieties as described for arrays.

Other bioassays are of use in the fields of proteomics, and the like. For example, cell function, both normal and pathologic, depends, in part, on the genes expressed by the cell (i.e., gene function). Gene expression has both qualitative and quantitative aspects. That is, cells may differ both in terms of the particular genes expressed and in terms of the relative level of expression of the same gene. Differential gene expression is manifested, for example, by differences in the expression of proteins encoded by the gene, or in post-translational modifications of expressed proteins. For example, proteins can be decorated with carbohydrates or phosphate groups, or they can be processed through peptide cleavage. Thus, at the biochemical level, a cell represents a complex mixture of organic biomolecules.

One goal of functional genomics ("proteomics") is the identification and characterization of organic biomolecules that are differentially expressed between cell types. By comparing expression, one can identify molecules that may be responsible for a particular pathologic activity of a cell. For example, identifying a protein that is expressed in cancer cells but not in normal cells is useful for diagnosis and, ultimately, for drug discovery and treatment of the pathology. Upon completion of the Human Genome Project, all the human genes will have been cloned, sequenced and organized in databases. In this "post-genome" world, the ability to identify differentially expressed proteins will lead, in turn, to the identification of the genes that encode them. Thus, the power of genetics can be brought to bear on problems of cell function.

Differential chemical analyses of gene expression and function require tools that can resolve the complex mixture of molecules in a cell, quantify them and identify them, even when present in trace amounts. The current tools of analytical chemistry for this purpose are presently limited in each of these areas. One popular biomolecular separation method is gel electrophoresis. Frequently, a first separation of proteins by isoelectric focusing in a gel is coupled with a second separation by sodium dodecyl sulfate-polyacrylamide gel electrophoresis (SDS-PAGE). The result is a map that resolves proteins according to the dimensions of isoelectric point (net charge) and size (i.e., mass). Although useful, this method is limited in several ways. First, the method provides information only about two characteristics of a biomolecule-mass and isoelectric point ("pI"). Second, the resolution power in each of the dimensions is limited by the resolving power of the gel. For example, molecules whose mass differ by less than about 5% or less than about 0.5 pI are often difficult to resolve. Third, gels have limited loading capacity, and thus limited sensitivity; one often cannot detect biomolecules that are expressed in small quantities. Fourth, small proteins and peptides with a molecular mass below about 10-20 kDa are not observed.

The use of mass spectrometric methods is replacing gels as the method of choice for bioassays. Efforts to improve the sensitivity of assays have resulted in the application of a number of mass spectrometric formats to the analysis of samples of biological relevance. In addition to the innovations in mass spectrometric techniques, substrates that adsorb an analyte ("chips") have also developed and the early designs have been improved upon.

Particularly useful methods of performing bioassays rely on the use of an adsorbent chip in conjunction with mass spectrometry. Prior investigators, have reported a variety of techniques for analyte detection using mass spectroscopy, but these techniques suffered because of inherent limitations in sensitivity and selectivity of the techniques, specifically including limitations in detection of analytes in low volume, undifferentiated samples (Hillenkamp, Bordeaux Mass Spectrometry Conference Report, pp. 354-62 (1988); Karas and Hillenkamp, Bordeaux Mass Spectrometry Conference Report, pp. 416-17 (1988); Karas and Hillenkamp, Analytical Chemistry, 60:2299 2301(1988); Karas, et al., Biomed. Environ. Mass Spectrum 18:841-843 (1989)). The use of laser beams in time-of-flight mass spectrometers is shown, for example, in U.S. Pat. Nos. 4,694,167; 4,686,366, 4,295, 046, and 5,045,694, incorporated herein by reference.

Exemplary mass spectrometric formats include matrix assisted laser desorption/ionization mass spectrometry (MALDI), see, e.g., U.S. Pat. No. 5,118,937 (Hillenkamp et al.) and U.S. Pat. No. 5,045,694 (Beavis and Chait), and surface enhanced laser desorption/ionization mass spectrometry (SELDI), see, e.g., U.S. Pat. No. 5,719,060 (Hutchens and Yip), incorporated herein by reference.

Direct laser desorption/ionization of biomolecules, such as polypeptides and nucleic acids, generally results in fragmentation of the biomolecules. To achieve desorption and ionization of intact biomolecules having weights into the hundreds-of-thousands of Daltons, various techniques have been used. In one methodology developed in the 1980's, referred to as MALDI, the biomolecules are mixed in solution with an energy absorbing organic molecule ("EAM"), referred to as a "matrix." The matrix is allowed to crystallize on a mass spectrometry probe, capturing biomolecules within the matrix. In SELDI, biomolecules are captured by adsorbents bound to a solid phase, and a matrix solution may then be applied to the captured biomolecules. Two very popular matrix materials are sinnapinic acid, which is preferred for use with large biomolecules such as proteins, and cyano hydroxyl cinammic acid, which is preferred for use with peptides and oligonucleotides.

There are a number of problems and limitations with prior matrices. For example, it is difficult to wash away contaminants present in analyte or matrix. Other problems include formation of analyte-salt ion adducts, less than optimum solubility of analyte in matrix, unknown location and concentration of analyte molecules within the solid matrix, signal (molecular ion) suppression "poisoning" due to simultaneous presence of multiple components, and selective analyte desorption/ionization.

Moreover, analysis by means of laser desorption/ionization time-of-flight mass spectrometry requires the preparation of a crystalline solid mixture of the protein or other analyte molecule in a large molar excess of matrix material deposited on the bare surface of a probe. Embedding the analyte in such a matrix is believed to be a necessary condition to prevent the destruction and fragmentation of analyte molecules by a desorption means, e.g., a laser beam. In other words, without the matrix the analyte molecules are easily fragmented by the laser energy and the mass, and identity, of the target macromolecule become very difficult or almost impossible to determine. Proper application of a large amount of matrix molecules over the analyte consistently each time an analysis is performed becomes a cumbersome task for a routine process. Importantly, a small amount of inconsistency in any of the required steps makes an accurate examination of analyte molecules almost impossible.

One notable attempt to overcome the deficiencies of known matrices relied upon chemically modifying the chip by binding small molecular EAM to the surface of the chip. See, for example, U.S. Pat. Nos. 6,027,942; 6,020,208; 6,124,137; and Hutchens and Yip, *Tetrahedron Lett.* 37: 5669-5672 (1996). The chemically modified chip is disclosed to be advantageous in analyses in which it is desired to modify or derivatize the analyte subsequent to its immobilization on the chip.

The prior methods, relying upon chemical derivatization of the chip substrate with small molecular EAM lacks versatility in a number of regards. For example, attachment of the EAM to the substrate requires the use of EAM and substrate materials having complementary reactive groups, thereby limiting the species that can be used for both the chip and substrate. Moreover, incomplete reaction between EAM and the chip substrate can interfere with the assay for which the chip is intended. For example, unreacted EAM may remain adventitiously, or reactive groups on the surface of the chip may remain unfunctionalized with an EAM. Unreacted EAM may itself be ionized during the mass spectrometric analysis, resulting in a high level of background or obscuring data from the analyte. Unfunctionalized groups on the chip may act as affinity moieties, adventitiously binding the analyte and hindering its desorption from the chip.

A matrix based upon an easily prepared and readily available EAM, that did not require chemical attachment to the substrate is desirable. If the matrix could also be assembled from a wide range of EAM, under a variety of conditions, this would represent a significant advance in the art. The present invention provides such a matrix, chips incorporating the matrix and methods of making and using the matrix.

BRIEF SUMMARY OF THE INVENTION

It has now been discovered that a matrix based on a polymer that incorporates subunits derived from monomeric energy absorbing molecules can be used in desorption/ionization mass spectrometric analyses. The matrix of the invention is unique in the unprecedented level of versatility available in both its structure and its manner of preparation. Moreover, the matrix of the invention enhances the accuracy of molecular detection, and the reproducibility of EAM distribution on an analytical device, such as a chip. Additionally, analyses using the polymeric EAM matrix of the invention involve significantly fewer steps to prepare and process the analyses, e.g., the chips can be manufactured with the polymeric matrix in place, obviating the necessity of pipetting matrix components onto the chip prior to performing an analysis.

In a first aspect, the present invention provides a polymerizable monomer that includes a polymerizable moiety and a photo-reactive group that includes an aryl nucleus having a substituent thereon. The substituent preferably includes a carbonyl or carboxyl group that is electronically conjugated to the π-system of the aryl nucleus.

In addition to the monomers, the present invention provides photo-reactive polymeric materials. The polymeric materials of the invention include a photo-reactive polymer that absorbs photo-irradiation from a high fluence source to generate thermal energy, and transfers the thermal energy to allow desorption and ionization of the analyte molecules. In one embodiment of the invention, the polymeric material is a homopolymer (optionally cross-linked) made from monomers comprising a moiety that absorbs the photo-irradiation and a polymerizable moiety such as a vinyl group or a methacryl group. In another embodiment the photo-reactive polymer is a heteropolymer (optionally cross-linked) comprising photo-reactive monomers and monomers comprising binding functionalities. In another embodiment, the polymeric material comprises a photo-reactive polymer and a polymer derivatized with binding functionalities.

The matrix of the invention is readily prepared by art-recognized polymerization methods. A solution of the monomer can be deposited onto the chip and subsequently polymerized or, alternatively, the monomer can be polymerized and the resulting polymer deposited onto the chip. The matrix can be a homopolymer of the EAM, a mixture of more than one EAM, or a mixture of one or more EAM and a monomer having a desired property (e.g., charge, hydrophilicity, hydrophobicity). Thus, according to the present invention it is possible to "tune" the properties of the matrix by varying the nature and concentration of the constituents of the polymeric matrix.

In addition to the chemical properties, the morphology of the polymer can be varied as well. For example, the polymer can be a film or it can be formed under suspension or emulsion polymerization conditions to form beads or particles of the matrix. Moreover, the polymer can be made non-porous, microporous, or macroporous materials by means of porogens.

The matrix is useful to prepare chips for desorption/ionization mass spectrometric analysis. Thus, in a first aspect, the invention provides a device that includes a substrate having a surface; and a polymeric material attached to the surface. The polymeric material is adapted to receive analyte molecules. Moreover, the polymeric material includes a photo-reactive polymer that absorbs photo-irradiation from a high fluence source to generate thermal energy, and transfers the thermal energy to allow desorption and ionization of the analyte molecules.

In another aspect, there is provided a device that includes a substrate having a surface. The device also includes a polymeric material that is in contact with surface. The polymeric material can be reversibly layered onto the surface or it can be immobilized by a binding modality. The polymeric material includes a photo-reactive polymer that absorbs photo-irradiation from a high fluence source to generate thermal energy, and transfers said thermal energy to allow desorption and ionization of an analyte in operative contact with said photo-reactive polymer.

Also provided is a method of preparing a chip of the invention. The method includes depositing onto a chip a polymer that includes an EAM having the analyte-receiving and energy absorption properties set forth above. The polymer can be formed prior to its deposition onto the chip or in situ on the chip. Thus, in an exemplary embodiment, the method includes contacting a surface of a substrate with a polymer precursor. The precursor includes a first photoreactive polymerizable monomer. The polymer precursor is polymerized, thereby forming a layer of a photo-reactive polymer. The resulting layer of photo-reactive polymer is optionally immobilized on the surface. In another exemplary embodiment.

In yet another aspect, the present invention provides a method of analyzing a sample. The method includes desorbing and ionizing the sample from a chip that included a polymeric matrix that includes an EAM. The matrix is a discrete polymer that is either formed prior to its deposition onto the chip or, alternatively, is formed in situ on the chip. This invention also provides other embodiments of co-polymerized, linear polymers. In one example, the composition is a co-polymer of α-cyano-4-methacryloyloxycinnamic acid and acrylate. In another embodiment, the composition is a co-polymer of α-cyano-4-methacryloyloxycinnamic acid, acrylate and 3-(tri-methoxy)silyl propyl methacrylate. In another embodiment, the composition is a co-polymer of α-cyano-4-methacryloyloxycinnamic acid and octadecylmethacrylate.

In a further aspect, the invention provides a kit. An exemplary kit includes a substrate. Also included is a polymerizable monomer that includes a polymerizable moiety; and a photo-reactive moiety. An exemplary photo-reactive moiety is an aryl nucleus having a substituent such as a carbonyl or carboxyl group conjugated to the 90-system of the aryl nucleus.

Other objects, advantages and aspects of the present invention will be apparent from the detailed description that follows.

DETAILED DESCRIPTION OF THE INVENTION

Abbreviations and Definitions

Figure 1:
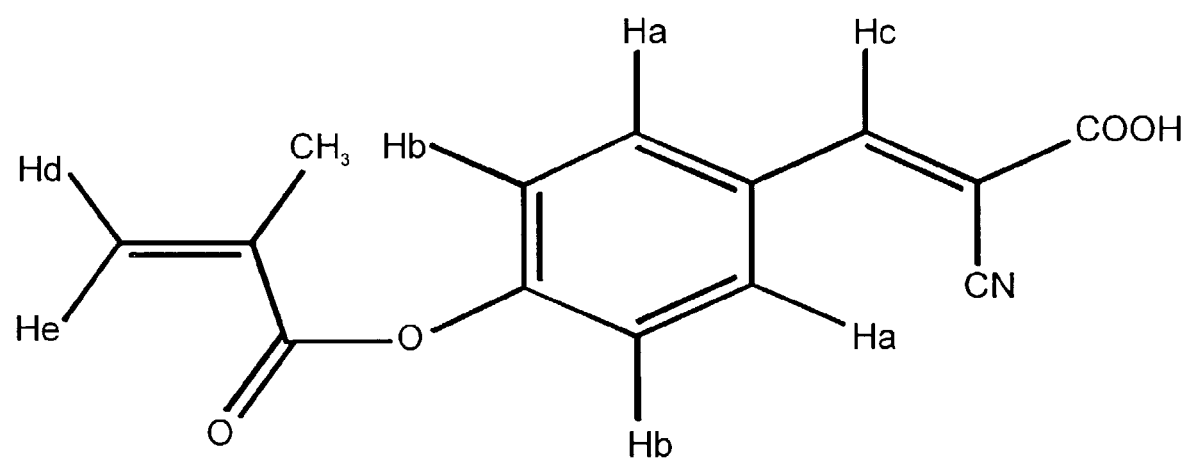
FIG. 1 correlates the $^1$H NMR peaks and structure of CHCAMA.

"CHCA," as used herein refers to α-cyano-4-hydroxycinnamic acid.

"CHCAMA," as used herein refers to α-cyano-4-methacryloyloxycinnamic acid. "Poly-CHCAMA," refers to a polymer incorporating a monomer derived from CHCAMA.

"DHBMA," as used herein refers to 2,5-dimethacryloyloxy benzoic acid. "Poly-DHBMA," refers to a polymer incorporating a monomer derived from DHBMA.

"DHAPheMA," as used herein refers to 2,6-dimethacryloyloxyacetophenone. "Poly-DHAPheMA," refers to a polymer incorporating a monomer derived from DHAPheMA.

"DEGDMA," as used herein refers to di(ethylene glycol) dimethylacrylate. "Poly-DEGDMA," refers to a polymer incorporating a monomer derived from DEGDMA.

As used herein, "MALDI" refers to Matrix-Assisted Laser Desorption/Ionization.

"SELDI," as used herein refers to Surface Enhanced for Laser Desorption/Ionization.

"SEND," as used herein refers to Surface Enhanced for Neat Desorption.

As used herein, "TOF" stands for Time-of-Flight.

As used herein, "MS" refers to Mass Spectrometry.

As used herein "MALDI-TOF MS" refers to Matrix-assisted laser desorption/ionization time-of-flight mass spectrometry.

As used herein, the term "energy absorbing molecule (moiety)" is a component of a "photo-reactive polymer."

As used herein, the term "operative contact," refers to a relationship between an analyte and a photo-reactive polymer or an energy absorbing moiety of a photo-reactive polymer in which the analyte can be desorbed from the polymer by energy transferred from an external source to the EAM.

As used herein, the term "analyte desorption/ionization" refers to converting an analyte into the gas phase as an ion.

The term "matrix" refers to a plurality of generally acidic, energy absorbing chemicals (e.g., nicotinic or sinapinic acid) that assist in the desorption (e.g., by laser irradiation) and ionization of the analyte into the gaseous or vapor phase as intact molecular ions.

As used herein, "energy absorbing molecule, or moiety (EAM)" refers to a light absorbing species that, when presented on the surface of a probe element (as in the case of SEND), facilitate the neat desorption of molecules into the gaseous or vapor phase for subsequent acceleration as intact molecular ions.

As used herein, "desorption" refers to the departure of analyte from the surface and/or the entry of the analyte into a gaseous phase.

As used herein, "ionization" refers to the process of creating or retaining on an analyte an electrical charge equal to plus or minus one or more electron units.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent —$S(O)_2HN$—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —$CO_2R'$, —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —$S(O)_2R'$, —$S(O)_2$NR'R", —$NRSO_2R'$, —CN and —$NO_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazol, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above.

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the aryl substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_{20}$)alkyl.

Each of the above terms is meant to include both substituted and unsubstituted forms of the indicated radical.

"Moiety" refers to the radical of a molecule that is attached to another moiety.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The symbol ∼∼∼, whether utilized as a bond or displayed perpendicular to a bond indicates the point at which the displayed moiety is attached to the remainder of the molecule, solid support, etc.

As used herein, the term "heteroatom" is meant to include oxygen (O), nitrogen (N), sulfur (S) and silicon (Si).

"Analyte," as utilized herein refers to the species of interest in an assay mixture. Exemplary analytes include, but are not limited to cells and portions thereof, enzymes, antibodies and other biomolecules, drugs, pesticides, herbicides, agents of war and other bioactive agents.

The term "substance to be assayed" as used herein means a substance, which is detected qualitatively or quantitatively by the process or the device of the present invention. Examples of such substances include antibodies, antibody fragments, antigens, polypeptides, glycoproteins, polysaccharides, complex glycolipids, nucleic acids, effector molecules, receptor molecules, enzymes, inhibitors and the like.

The term, "assay mixture," refers to a mixture that includes the analyte and other components. The other components are, for example, diluents, buffers, detergents, and contaminating species, debris and the like that are found mixed with the analyte. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid but, which functions in a manner similar to a naturally occurring amino acid.

"Therapeutic agent" or "drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "therapeutic agent" and "drug" encompass both the inactive drug and the active metabolite.

The term "binding functionality" as used herein means a moiety, which has an affinity for a certain substance such as a "substance to be assayed," that is, a moiety capable of interacting with a specific substance to immobilize it on the chip of the invention. Binding functionalities of use in practicing the present invention are generally. Chromatographic binding functionalities bind substances via charge-charge, hydrophilic-hydrophilic, hydrophobic-hydrophobic, van der Waals interactions and combinations thereof. Biospecific binding functionalities generally involve complementary 3-dimensional structures involving one or more of the above interactions.

The term "detection means" as used herein refers to detecting a signal produced by the immobilization of the substance to be assayed onto the binding functionality by visual judgment or by using an appropriate external measuring instrument depending on the signal properties.

The term "attached," and "immobilized" are used interchangeably herein and they encompass interactions including, but not limited to, covalent bonding, ionic bonding, electrostatic interactions, hydrogen bonding, hydrophobic-hydrophobic interaction, hydrophilic-hydrophilic interaction, chemisorption, physisorption and combinations thereof.

The term "independently selected" is used herein to indicate that the groups so described can be identical or different.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

The term "biological material" refers to any material derived from an organism, organ, tissue, cell or virus. This includes biological fluids such as saliva, blood, urine, lymphatic fluid, prostatic or seminal fluid, milk, etc., as well as extracts of any of these, e.g., cell extracts, cell culture media, fractionated samples, or the like.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer which uses laser as a means to desorb, volatilize, and ionize an analyte.

"Tandem mass spectrometer" refers to any mass spectrometer that is capable of performing two successive stages of m/z-based discrimination or measurement of ions, including of ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that are capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, and Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionuclides (used in plasma desorption); and (4) primary ions generating secondary ions (used in secondary ion mass spectrometry). The preferred form of ionizing energy for solid phase analytes is a laser (used in laser desorption/ ionization), in particular, nitrogen lasers, Nd-Yag lasers, ErYAG lasers, NdYAG, $CO_2$ lasers, tunable OPO lasers and other pulsed laser sources.

"Fluence" refers to the laser energy delivered per unit area of interrogated image. Typically, a sample is placed on the surface of a probe, the probe is engaged with the probe interface and the probe surface is struck with the ionizing energy. The energy desorbs analyte molecules from the surface into the gas phase and ionizes them. As used herein, the term "high fluence", refers to a fluence of from about 1 $mJ/mm^2$ to 50 mj/mm2. Various lasers and some high intensity plasma discharge lamps qualify can be used to provide energy of "high fluence."

Other forms of ionizing energy for analytes include, for example: (1) electrons which ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Probe" in the context of this invention refers to a device that can be used to introduce ions derived from an analyte into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" is a method of gas phase ion spectrometry (e.g., mass spectrometry) in which the surface of the probe that presents the analyte to the energy source plays an active role in desorption/ionization of analyte molecules. SELDI technology is described in, e.g., U.S. Pat. No. 5,719,060 (Hutchens and Yip) and U.S. Pat. No. 6,225,047 (Hutchens and Yip).

One version of SELDI, called Surface-Enhanced Neat Desorption or "SEND" involves the use of probes comprising energy absorbing molecules chemically bound to the probe surface. ("SEND probe.") "Energy absorbing molecules" ("EAM") refer to molecules that are capable of absorbing energy from a laser desorption ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI.

Another version of SELDI, called "Surface-Enhanced Affinity Capture" or "SEAC" involves the use of probes comprising an adsorbent (also called a "capture reagent") attached to the surface. ("SEAC probe.") "Adsorbent surface" refers to a surface to which an adsorbent is bound. "Chemically selective surface" refers to a surface to which is bound either an adsorbent (capture reagent) or a reactive moiety that is capable of binding a capture reagent, e.g., through a reaction forming a covalent or coordinate covalent bond.

"Adsorbent" or "binding functionality" refers to any material capable of binding an analyte (e.g., a target polypeptide). "Chromatographic adsorbent" refers to a material typically used in chromatography. Chromatographic adsorbents include, for example, ion exchange materials, metal chelators, hydrophobic interaction adsorbents, hydrophilic interaction adsorbents, dyes, mixed mode adsorbents (e.g., hydrophobic attraction/electrostatic repulsion adsorbents). "Biospecific adsorbent" refers an adsorbent comprising a biomolecule, e.g., a nucleotide, a nucleic acid molecule, an amino acid, a polypeptide, a simple sugar, a polysaccharide, a fatty acid, a lipid, a steroid or a conjugate of these (e.g., a glycoprotein, a lipoprotein, a glycolipid). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than a chromatographic adsorbent. Further examples of adsorbents for use in SELDI can be found in U.S. Pat. No. 6,225,047 (Hutchens and Yip, "Use of retentate chromatography to generate difference maps," May 1, 2001).

"Reactive moiety" refers to a chemical moiety that is capable of binding a capture reagent. Epoxide and carbodiimidizole are useful reactive moieties to covalently bind polypeptide capture reagents. Nitrilotriacetic acid is a useful reactive moiety to bind metal chelating agents through coordinate covalent bonds.

"Adsorption" refers to detectable non-covalent binding of an analyte to an adsorbent or capture reagent.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Polymerizable moiety" refers to a functional group that is capable of participating in a polymerization reaction and, through the polymerization reaction, be converted into a component of a polymer. Representative "polymerizable moieties" include, but are not limited to, vinyl, acryloyl, carboxylic acids and esters, anhydrides, aldehydes, ureas, etc. Additional "polymerizable moieties" are known to those of skill in the art. See, for example, Seymour, R. et al., POLYMER CHEMISTRY 2nd Ed., Marcel Dekker, Inc., New York, 1988.

Introduction

The present invention provides a polymeric energy absorbing matrix that is appropriate for use, inter alia, in conjunction with desorption/ionization modes of mass spectrometric analysis. The properties of the matrix of the invention can be tuned by varying the structure of the monomers utilized in forming the polymeric matrix. For example, the concentration of EAMs within the matrix can be varied to provide the appropriate density of energy-absorbing molecules bonded (covalently or noncovalently) such that the energy-absorbing molecules can be used to facilitate the desorption of analyte molecules of varying masses. The optimum ratio of adsorbed or bonded energy-absorbing molecules to analyte generally varies with the mass of the analyte to be detected. Moreover, the invention provides a matrix in which the energy absorbing molecules are combined with affinity reagents ("binding functionalities"), both chemical and/or biological, for the specific purpose of capturing (adsorbing) specific analyte molecules or classes of analyte molecules for the subsequent preparation, modification, and desorption of the analyte molecules.

A still further object is to provide a method and apparatus for desorption and ionization of analytes in which unused portion of the analytes contained on the presenting surface remain chemically accessible, so that a series of chemical and/or enzymatic or other treatments (e.g., discovery of analyte-associated molecules by molecular recognition) of the analyte may be conducted on the chip of the invention, followed by sequential analyses of the modified analyte by mass spectrometry or other detection means. The subsequent modifications of the analyte can be used to elucidate primary, secondary, tertiary, or quaternary structure of the analyte and its components.

In the sections that follow, the polymeric matrix of the invention is described. The use of the matrix in an analytical device, as exemplified by a chip for mass spectrometric analysis is also illustrated. Moreover, methods of using the polymeric matrix to produce an analytical device are set forth, as are methods of using the analytical device to detect, quantify, or otherwise characterize an analyte.

The Monomers

In a first aspect, the present invention provides a polymerizable monomer that includes a polymerizable moiety and a photo-reactive group that includes an aryl nucleus having a substituent thereon. The substituent preferably includes a carbonyl or carboxyl group that is electronically conjugated to the π-system of the aryl nucleus.

In certain exemplary embodiments, the monomers of the invention have a structure such as that set forth below:

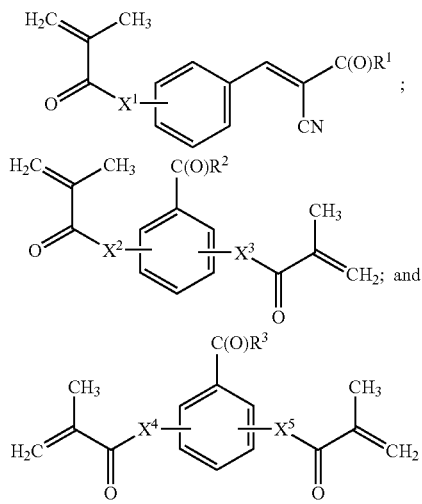

in which the symbols $R^1$, $R^2$ and $R^3$ represent members independently selected from H, $NR^4R^5$, $OR^6$, substituted or unsubstituted alkyl, substituted or unsubstituted heteroalkyl and substituted or unsubstituted aryl. The symbols $X^1$, $X^2$ and $X^3$ represent members independently selected from the group consisting of O, $NR^7R^8$ and S. The symbols $R^4$, $R^5$, $R^6$, $R^7$, and R8 represent members independently selected from the group consisting of H, substituted or unsubstituted alkyl, substituted or unsubstituted heteroalkyl and substituted or unsubstituted aryl.

In a presently preferred embodiment, the polymerizable monomer of the invention is α-cyano-4-methacryloyloxycinnamic acid, 2,5-dimethacryloyloxybenzoic acid or 2,6-dimethacryloyloxyacetophenone.

The Matrix

As discussed previously, the present invention provides a polymeric matrix that includes a subunit derived from an EAM. Few structural restrictions are placed upon the EAMs useful in practicing the present invention. In its most general embodiment, the matrix of the invention includes an EAM that absorbs photo-irradiation from a high fluence source (e.g., laser, flash lamp) to generate thermal energy, and transfers the thermal energy to allow desorption and ionization of an analyte molecule that is in contact or proximate to the EAM. The EAM can be an integral, covalently bonded component of the polymer, or it can be a species that is entrained within a polymeric matrix. When the EAM is not covalently bonded to the polymer it preferably interacts with the polymer via electrostatic, ionic, hydrophilic, or hydrophobic attraction. The EAM may also be entrained within the polymer by virtue of its being too large to diffuse from or otherwise exit the polymer.

The EAMs of use in practicing the present invention will generally be based upon a homoaromatic or heteroaromatic nucleus. One of skill will appreciate that appropriate nuclei include monocylic (e.g., benzene, pyridine, pyrrole, furan, thiophene) as well as polycyclic systems. Moreover, when the aromatic nucleus is polycyclic, the ring system can be fused (e.g., naphthalene, benzofuran), or bonded in another fashion (e.g., biphenyl).

The aromatic nucleus is functionalized with a polymerizable moiety that is a reactive functional group. Those of skill will appreciate that an array of functional groups are appropriate for polymerizing monomers, and the present invention is not limited by the nature of the polymerizable functionality. Representative polymerizable reactive functional groups are set forth below.

Exemplary reactive functional groups (e.g., $X^1$ and $X^2$) include:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated or alkylated;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with reactions in which they are not intended to participate. Alternatively, the reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Those of skill in the art will understand that the reactive functional groups discussed herein represent only a subset of functional groups that are useful in assembling the matrix of the invention.

In a particularly preferred embodiment, the reactive functional group includes an unsaturated carbon-carbon or carbon-heteroatom bond. In a still further preferred embodiment, the reactive functional group includes at least one vinyl group, which is suitable for polymerization.

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., N March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-$O_2$, and 828; for hydroxymethyl ketone esters, see, Petracek et al. *Annals NY Acad. Sci.*, 507:353-54 (1987); for disulfides, see, March supra at 1160; and for phosphonate esters and phosphonamidates, see, e.g., copending application Ser. No. 07/943,805, which is expressly incorporated herein by reference.

In certain embodiments, one or more of the active groups are protected during one or more steps of the reaction to assemble the dendrimer or a conjugate of the dendrimer. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In an exemplary embodiment, the matrix of the invention is based upon a phenyl nucleus. Representative examples of matrix components are moieties that include an aryl nucleus having a substituent thereon. The substituent preferably includes a π-system. Even more preferred are substituents in which the π-system is conjugated to the π-system of the aryl nucleus. Exemplary substituents of use in the matrix of the invention include carbonyl and carboxyl groups conjugated to the π-system of the aryl nucleus.

In a representative embodiment, the matrix includes an EAM having the structure:

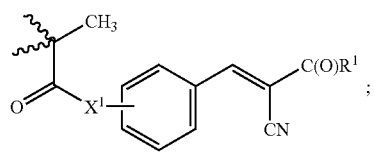

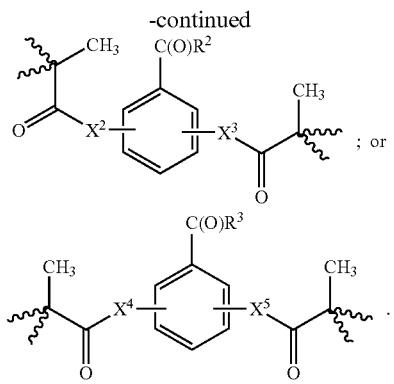

In the formulae above, the symbols $R^1$, $R^2$ and $R^3$ represent members independently selected from H, $-NR^4R^5$, $-OR^6$, substituted or unsubstituted alkyl, substituted or unsubstituted heteroalkyl and substituted or unsubstituted aryl. $X^1$, $X^2$ and $X^3$ represent members independently selected from O, $NR^7R^8$ and S. The symbols $R^4$, $R^5$, $R^6$, $R^7$, and $R^8$ are members independently selected from H, substituted or unsubstituted alkyl, substituted or unsubstituted heteroalkyl and substituted or unsubstituted aryl.

Exemplary components of the polymer that are encompassed by the generic structures set forth above include, include subunits derived from α-cyano-4-methacryloyloxycinnamic acid, 2,5-dimethacryloyloxybenzoic acid, 2,6-dimethacryloyloxyacetophenone and combinations thereof.

In certain embodiments, it is preferred to crosslink a percentage of the EAM of the matrix with a crosslinking agent. The crosslinking agent is used to "tune" the properties of the matrix. Any cross-linking agent, useful to crosslink the EAM can be used to prepare the matrix of the invention. In a preferred embodiment, the crosslinking agent is a polymerizable monomer. Preferred addition polymerizable crosslinking precursors include: ethylene glycol dimethacrylate (EGDMA); ethylene glycol diacrylate (EGDA); propylene glycol dimethacrylate; propylene glycol diacrylate; butylene glycol dimethacrylate; butylene glycol diacrylate; hexamethylene glycol dimethacrylate; hexamethylene glycol diacrylate; pentamethylene glycol diacrylate; pentamethylene glycol dimethacrylate; decamethylene glycol diacrylate; decamethylene glycol dimethacrylate; vinyl acrylate; divinyl benzene; glycerol triacrylate; trimethylolpropane triacrylate; pentaerythritol triacrylate; polyoxyethylated trimethylolpropane triacrylate and trimethacrylate and similar compounds as disclosed in U.S. Pat. No. 3,380,831; 2,2-di(p-hydroxyphenyl)-propane diacrylate; pentaerythritol tetraacrylate; 2,2-di-(p-hydroxyphenyl)-propane dimethacrylate; triethylene glycol diacrylate; polyoxyethyl-2,2-di-(p-hydroxyphenyl)-propane dimethacrylate; di-(3-methacryloxy-2-hydroxypropyl)ether of bisphenol-A; di-(2-methacryloxyethyl)ether of bisphenol-A; di-(3-acryloxy-2-hydroxypropyl)ether of bisphenol-A; di-(2-acryloxyethyl) ether of bisphenol-A; di-(3-methacryloxy-2-hydroxypropyl) ether of tetrachloro-bisphenol-A; di-(2-methacryloxyethyl) ether of tetrachloro-bisphenol-A; di-(3-methacryloxy-2-hydroxypropyl)ether of tetrabromo-bisphenol-A; di-(2-methacryloxyethyl)ether of tetrabromo-bisphenol-A; di-(3-methacryloxy-2-hydroxypropyl)ether of 1,4-butanediol; di-(3-methacryloxy-2-hydroxypropyl)ether of diphenolic acid; triethylene glycol dimethacrylate; polyoxypropyl one trimethylol propane triacrylate (462); 1,2,4-butanetriol trimethacrylate; 2,2,4-trimethyl-1,3-pentanediol dimethacrylate; pentaerythritol trimethacrylate; 1-phenyl ethylene-1,2-dimethacrylate; pentaerythritol tetramethacrylate; trimethylol propane trimethacrylate; 1,5-pentanediol dimethacrylate; diallyl fumarate; 1,4-benzenediol dimethacrylate; 1,4-diisopropenyl benzene; and 1,3,5-triisopropenyl benzene.

An exemplary class of addition polymerizable crosslinking precursors are an alkylene or a polyalkylene glycol diacrylate or dimethacrylate prepared from an alkylene glycol of 2 to 15 carbons or a polyalkylene ether glycol of 1 to 10 ether linkages, and those disclosed in U.S. Pat. No. 2,927,022, e.g., those having a plurality of addition polymerizable ethylenic linkages particularly when present as terminal linkages. Members of this class are those wherein at least one and preferably most of such linkages are conjugated with a double bonded carbon, including carbon double bonded to carbon and to such heteroatoms as nitrogen, oxygen and sulfur. Also included are such materials wherein the ethylenically unsaturated groups, especially the vinylidene groups, are conjugated with ester or amide structures and the like.

The matrix of the invention can also include a binding functionality for an analyte within its polymeric structure. For purposes of convenience, both the binding functionality and components of the binding functionality are referred to as the binding functionality. The binding functionality is selected from an electrostatic functionality, a hydrophobic functionality, a hydrogen bonding functionality, a coordinate covalent bonding functionality, a covalent bonding functionality, a biospecific bonding functionality and combinations thereof.

In an exemplary embodiment, the binding functionality comprises an organic functional group that interacts with a component of the analyte. In an exemplary embodiment, the organic functional group is selected from simple groups, such as amines, carboxylic acids, sulfonic acids, alcohols, sulfhydryls and the like. Functional groups presented by more complex species are also of use, such as those presented by drugs, chelating agents, crown ethers, cyclodextrins, and the like. In an exemplary embodiment, the binding functionality is an amine that interacts with a structure on the analyte that binds to the amine (e.g., carbonyl groups, alkylhalo groups), or which protonates the amine (e.g., carboxylic acid, sulfonic acid) to form an ion pair. In another exemplary embodiment, the binding functionality is a carboxylic acid, which interacts with the analyte by complexation (e.g., metal ions), or which protonate a basic group on the analyte (e.g. amine) forming an ion pair.

The organic functional group can also be a component of a small organic molecule with the ability to specifically recognize an analyte molecule. Exemplary small organic molecules include, but are not limited to, amino acids, biotins, carbohydrates, glutathiones, and nucleic acids.

Exemplary amino acids suitable as binding functionalities, include L-alanine, L-arginine, L-asparagine, L-aspartic acid, L-cysteine, L-cystine, L-glutamic acid, L-glutamine, glycine, L-histidine, L-isoleucine, L-lysine, L-methionine, L-phenylalanine, L-proline, L-serine, L-threonine, L-thyroxine, D-tryptophan, L-tryptophan, L-tyrosine and L-valine. Typical avidin-biotin ligands include avidin, biotin, desthiobiotin, diaminobiotin, and 2-iminobiotin. Typical carbohydrates include glucoseamines, glycopryranoses, galactoseamines, the fucoseamines, the fucopyranosylamines, the galactosylamines, the glycopyranosides, and the like. Typical glutathione ligands include glutathione, hexylglutathione, and sulfobromophthalein-S-glutathione.

In another exemplary embodiment, the binding functionality is a biomolecule, e.g., a natural or synthetic peptide, antibody, nucleic acid, saccharide, lectin, receptor, antigen, cell or a combination thereof. Thus, in an exemplary embodiment, the binding functionality is an antibody raised against an analyte or against a species that is structurally analogous to an analyte. In another exemplary embodiment, the binding functionality is avidin, or a derivative thereof, which binds to a biotinylated analogue of the analyte. In still another exemplary embodiment, the binding functionality is a nucleic acid, which binds to single- or double-stranded nucleic acid analyte having a sequence complementary to that of the binding functionality.

Biomolecules useful in practicing the present invention are derived from any source. The biomolecules can be isolated from natural sources or they can be produced by synthetic methods. Proteins can be natural proteins, mutated proteins or fusion proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal.

Binding functionalities, which are antibodies can be used to recognize analytes which include, but are not limited to, proteins, peptides, nucleic acids, saccharides or small molecules such as drugs, herbicides, pesticides, industrial chemicals, organisms, cells and agents of war. Methods of raising antibodies against specific molecules or organisms are well known to those of skill in the art. See, U.S. Pat. No. 5,147,786, issued to Feng et al. on Sep. 15, 1992; U.S. Pat. No. 5,334,528, issued to Stanker et al. on Aug. 2, 1994; U.S. Pat. No. 5,686,237, issued to Al-Bayati, M. A. S. on Nov. 11, 1997; and U.S. Pat. No. 5,573,922, issued to Hoess et al. on Nov. 12, 1996.

Antibodies and other peptides can be attached to the adsorbent film by any known method. For example, peptides can be attached through an amine, carboxyl, sulfhydryl, or hydroxyl group. The site of attachment can reside at a peptide terminus or at a site internal to the peptide chain. The peptide chains can be further derivatized at one or more sites to allow for the attachment of appropriate reactive groups onto the chain. See, Chrisey et al. *Nucleic Acids Res.* 24:3031-3039 (1996). Methods for attaching antibodies to surfaces are also known in the art. See, Delamarche et al. *Langmuir* 12:1944-1946 (1996).

In another exemplary embodiment, the chip of this invention is an oligonucleotide array in which the binding functionality at each addressable location in the array comprises a nucleic acid having a particular nucleotide sequence. In particular, the array can comprise oligonucleotides. For example, the oligonucleotides could be selected so as to cover the sequence of a particular gene of interest. Alternatively, the array can comprise cDNA or EST sequences useful for expression profiling.

In another exemplary embodiment, the binding functionality is a drug moiety or a pharmacophore derived from a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds, which are being screened for their ability to interact with an analyte of choice. As such, drug moieties, which are useful in practicing the instant invention include drugs from a broad range of drug classes having a variety of pharmacological activities.

Exemplary classes of useful agents include, but are not limited to, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, aminone and dobutamine); antihypertensive drugs (e.g., enalapril, clonidine, hydralazine, minoxidil, guanadrel, guanethidine);diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), anti-metabolites (e.g., fluorouracil, methotrexate, mercaptopurine, thioguanine).

The binding functionality can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful binding functionalities include immunomodulating drugs (e.g., antihistamines, mast cell stabilizers, such as Iodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the binding functionality is a chelating agent, crown ether or cyclodextrin, host-guest chemistry will dominate the interaction between the binding functionality and the analyte. The use of host-guest chemistry allows a great degree of affinity-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge,1989; Dugas, H., BIOORGANIC CHEMISTRY; Springer-Verlag, New York, 1989, and references contained therein.

Additionally, a number of routes allowing the attachment of chelating agents, crown ethers and cyclodextrins to other molecules are available to those of skill in the art. See, for example, Meares et al., "Properties of In vivo Chelate-Tagged Proteins and Polypeptides." In, "MODIFICATION OF PROTEINS: FOOD, NUTRITIONAL, AND PHARMACOLOGICAL ASPECTS;" Feeney, R. E., Whitaker, J. R., Eds., American Chemical Society, Washington, D.C., 1982, pp.370-387; Kasina et al. *Bioconjugate Chem.* 9:108-117 (1998); Song et al., *Bioconjugate Chem.* 8:249-255 (1997).

In an exemplary embodiment, the binding functionality is a polyaminocarboxylate chelating agent such as ethylenediaminetetraacetic acid (EDTA) or diethylenetriaminepentaacetic acid (DTPA), which is attached to an amine on the substrate, or spacer arm, by utilizing the commercially available dianhydride (Aldrich Chemical Co., Milwaukee, Wis.). When complexed with a metal ion, the metal chelate binds to tagged species, such as polyhistidyl-tagged proteins, which can be used to recognize and bind analyte species. Alternatively, the metal ion itself, or a species complexing the metal ion can be the analyte.

In a further exemplary embodiment, the binding functionality forms an inclusion complex with the analyte of interest. In a preferred embodiment, the binding functionality is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978. Cyclodextrins are able to form inclusion complexes with an array of organic molecules including, for example, drugs, pesticides, herbicides and agents of war. See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al. *J. Chromatogr. A* 793:153-164 (1998). The cyclodextrin binding functionality can be attached to a spacer arm or directly to the substrate. See, Yamamoto et al., *J. Phys. Chem. B* 101:6855-6860 (1997). Methods to attach cyclodextrins to other molecules are well known to those of skill in the chromatographic and pharmaceutical arts. See, Sreenivasan, K. J. *Appl. Polym. Sci.* 60:2245-2249 (1996).

In a further preferred embodiment, the binding functionality is selected from nucleic acid species, such as aptamers and aptazymes that recognize specific analytes.

Preparation of the Matrix

In its most general aspect, the preparation of the matrix involves the selection of an appropriate polymerizable EAM monomer and the polymerization of that monomer to form either a homo- or co-polymer, which can either be a linear polymer or a cross-linked polymer. The polymerizable EAM monomer may be a commercially available monomer or it can be prepared according to methods readily accessible to those of skill in the art. The polymerizable EAM generally comprises an EAM moiety and a polymerizable moiety. Polymerizable moieties are well known in the art and include, for example vinyl, acryl and allyl groups and their derivatives.

By way of example, a representative scheme leading to the preparation of a polymerizable CHCA monomer is set forth in Scheme 1.

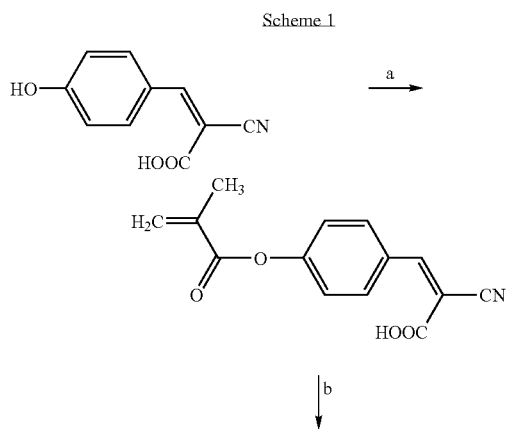

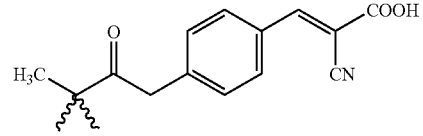

Figure 2:
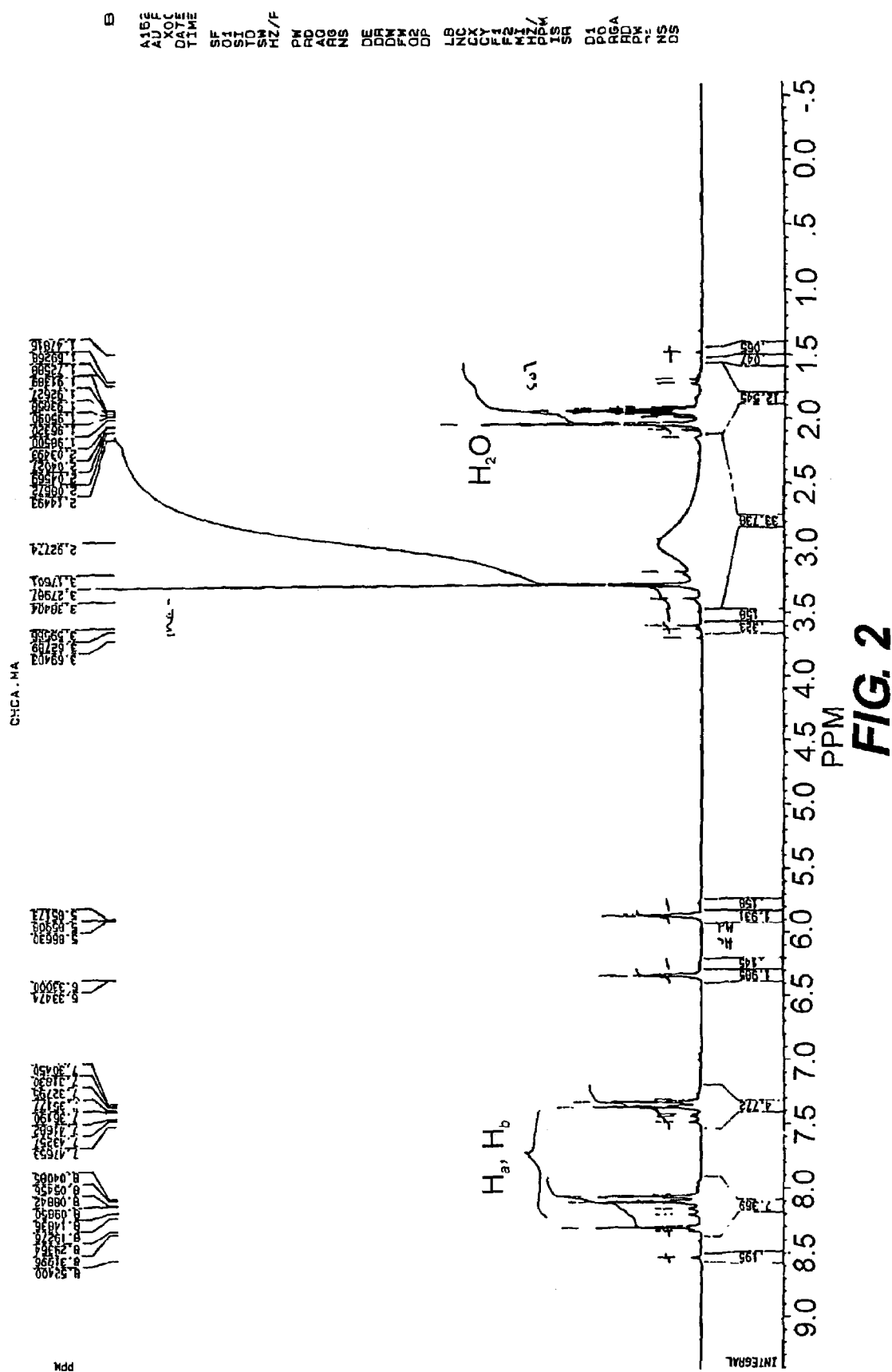
FIG. 2 is the $^1$H NMR spectrum of CHCAMA.

In Scheme 1, the aromatic nucleus is functionalized with a radical that includes a polymerizable, such as the methacryloyl group. In step a, α-cyano-4-hydroxycinnamic acid is treated with methacyrloyl chloride under Shotten-Baumann conditions (e.g., KOH, acetone/$H_2O$). The monomer is purified by standard methods including, but not limited to, crystallization, precipitation, chromatography (e.g., flash, HPLC, TLC), and the like. Characterization of the monomer is similarly performed by art-recognized methods, e.g., NMR, melting point, elemental analysis, etc. The $^1$H NMR spectrum and a table correlating the NMR peak positions with protons of the compound are set forth in FIG. 2 and FIG. 1, respectively.

In step b, the methacryloyloylated compound is homopolymerized or copolymerized. In certain embodiments, co-polymerization proceeds with a crosslinking agent, such as poly(ethylene glycol)dimethacrylate, to form a cross-linked polymer. The polymerization is initiated by the addition of a peroxide, such as lauroyl peroxide. The polymer is purified by methods known in the art, e.g., extraction of unreacted monomers, precipitation, crystallization, fractional crystallization, size exclusion chromatography, dialysis and the like. The polymer is also characterized by art-recognized methods, e.g., NMR, IR, size exclusion chromatography, elemental analysis and the like.

This invention contemplates both linear and cross-linked energy absorbing polymers. The linear polymers of this invention can be homo-polymers or co-polymers. Co-polymers provide several advantages, including the incorporation of different energy absorbing molecules, the spacing apart of energy absorbing monomers with "spacer monomers" ("spacer monomeric subunits") that do not absorb the same wavelengths of energy, and the incorporation of monomers incorporating binding functionalities.

For example, an energy absorbing monomer, such as CHCA-MA can be co-polymerized with a second energy absorbing monomer, such as trans-3,5-dimethoxy-4-acryloyloxycinnamic acid. Also, an energy absorbing monomer, such as CHCA-MA can be co-polymerized with spacer monomer, such as acrylic acid or methacrylaic acid.

In another example, the energy absorbing monomer can be co-polymerized with a monomer comprising a binding functionality. In one embodiment of this invention, the binding functionality has hydrophobic properties. More specifically, the monomer comprising a binding functionality can be octadecyl-methacrylate.

The cross-linked polymers of this invention are co-polymers comprising an energy absorbing monomer and a cross-linking monomer. For example, such a cross-linked polymer can comprise CHCA-MA and bis-acrylamide. It will be apparent that cross-linked polymers can be co-polymerized to include second energy absorbing monomers, spacer monomers and/or monomers comprising binding functionalities.

As will be discussed in more detail below, this invention contemplates using linear or cross-linked polymers either tethered to the surface of a substrate through covalent or other chemical bonds, or applied to the surface of a substrate, either before or after mixing with a sample. When the polymer comprises a binding functionality, the polymer can be washed to remove unbound molecules after contact with the sample.

Figure 4:
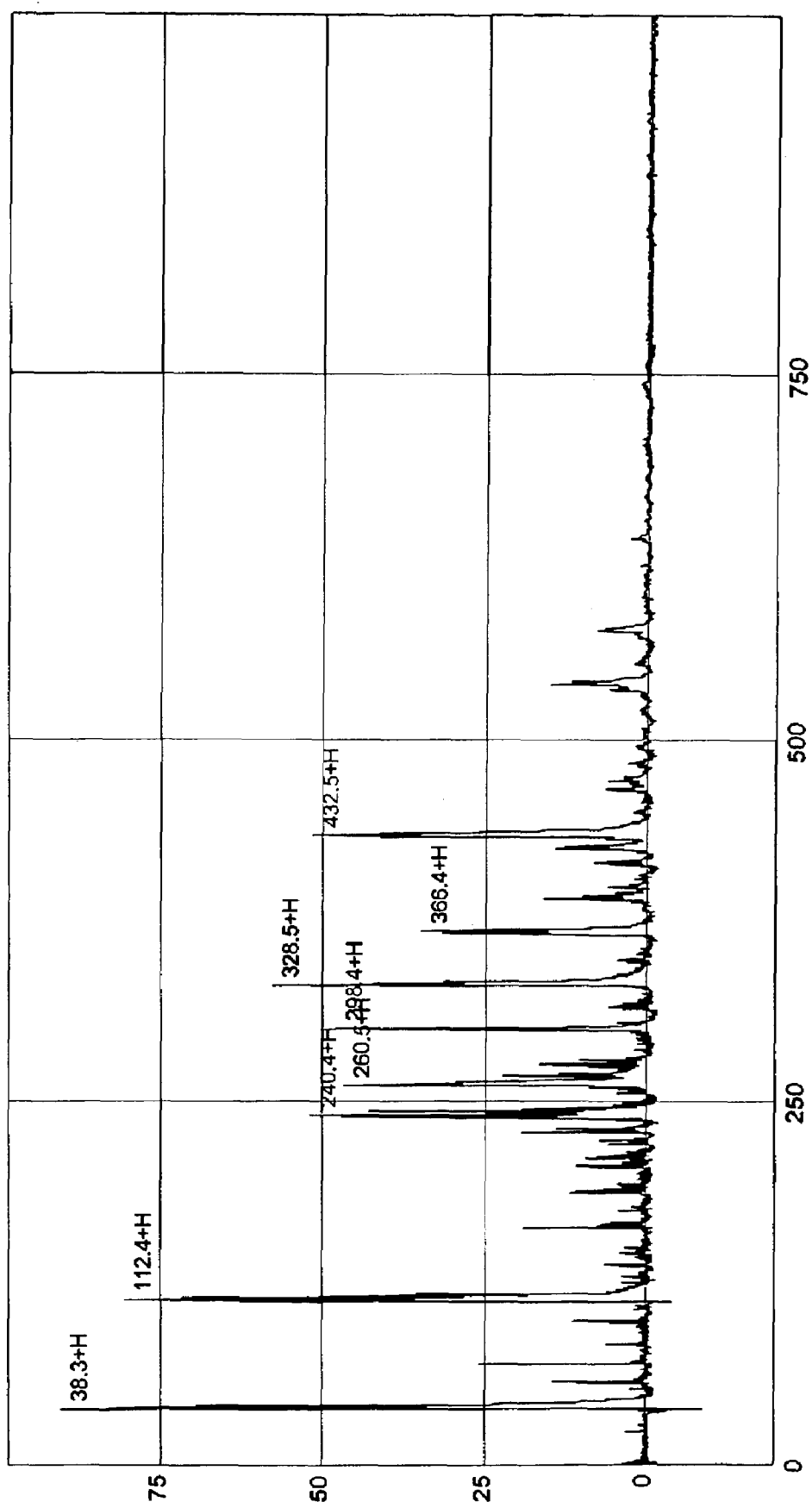
FIG. 4 is a mass spectrum of a peptide mixture, which was acquired using poly-DHBMA on a gold chip.
Figure 5:
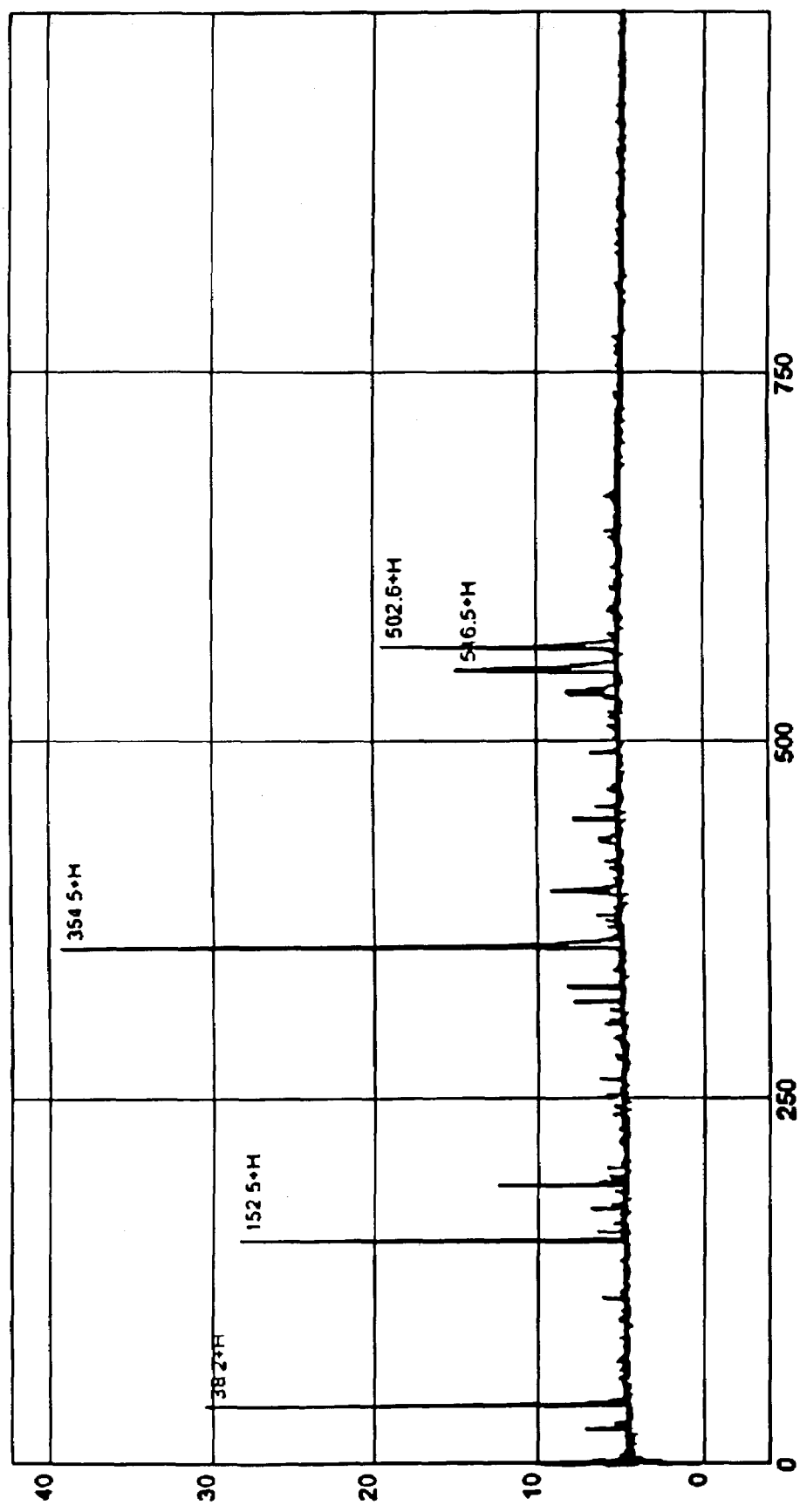
FIG. 5 is a mass spectrum of a peptide mixture, which was acquired using poly-DHAPheMA on a gold chip.
Figure 7:
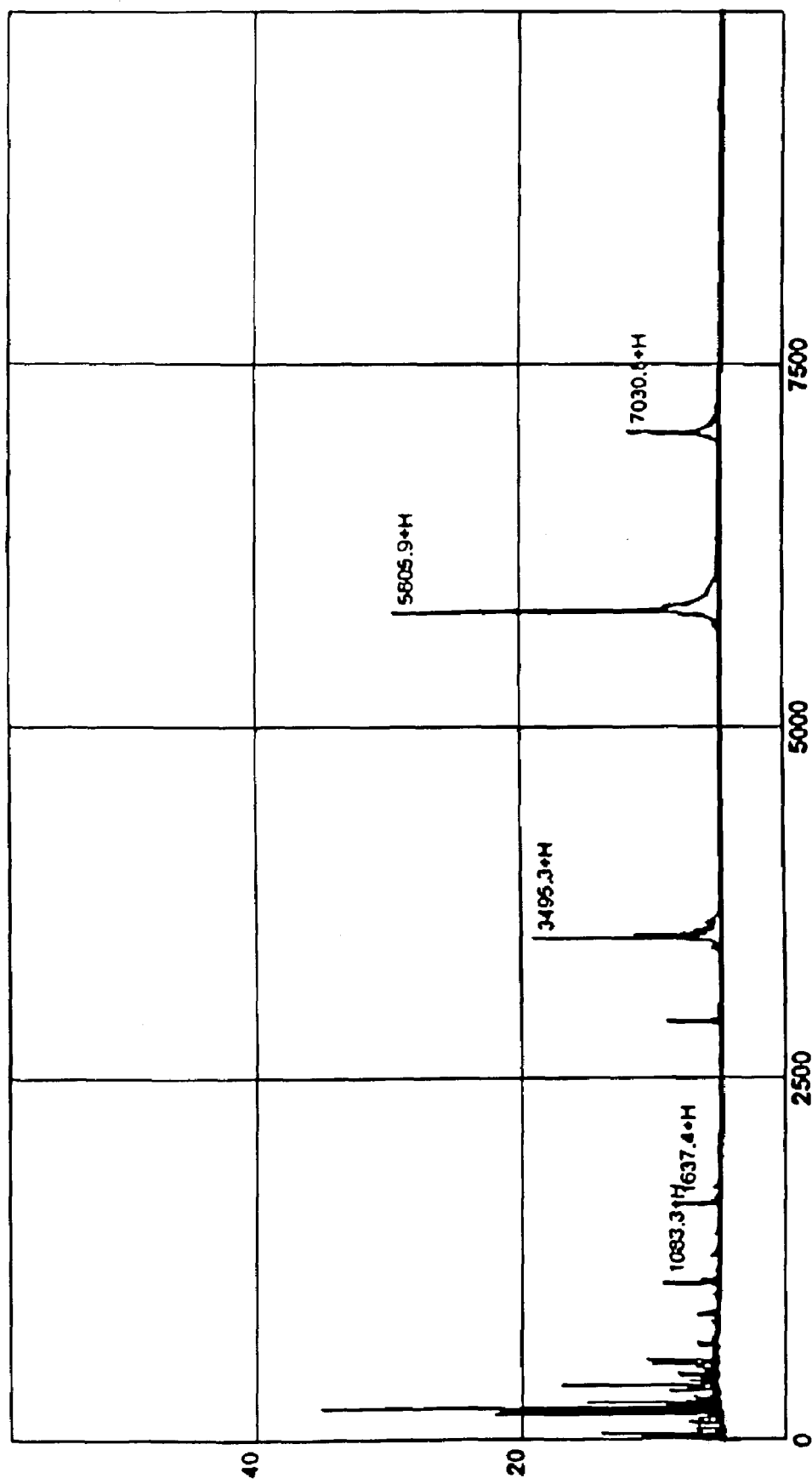
FIG. 7 is a mass spectrum of a peptide mixture, which was acquired using a cross-linked polymer poly-DEGDMA-CHCAMA on a gold chip.
Figure 8:
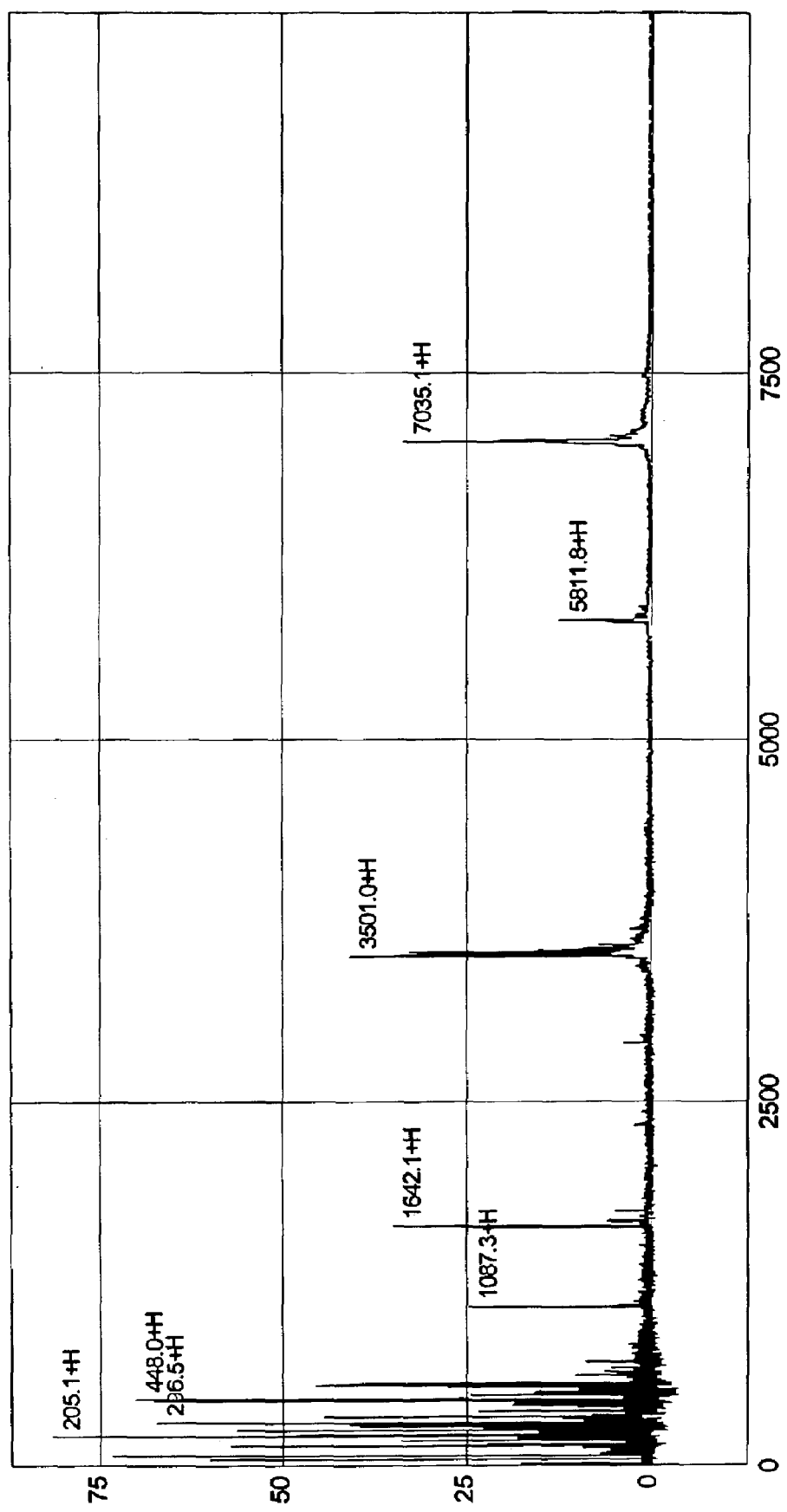
FIG. 8 is a mass spectrum of a peptide mixture, which was acquired using a copolymer poly-CHCAMA/DHBMA on a gold chip.
Figure 11:
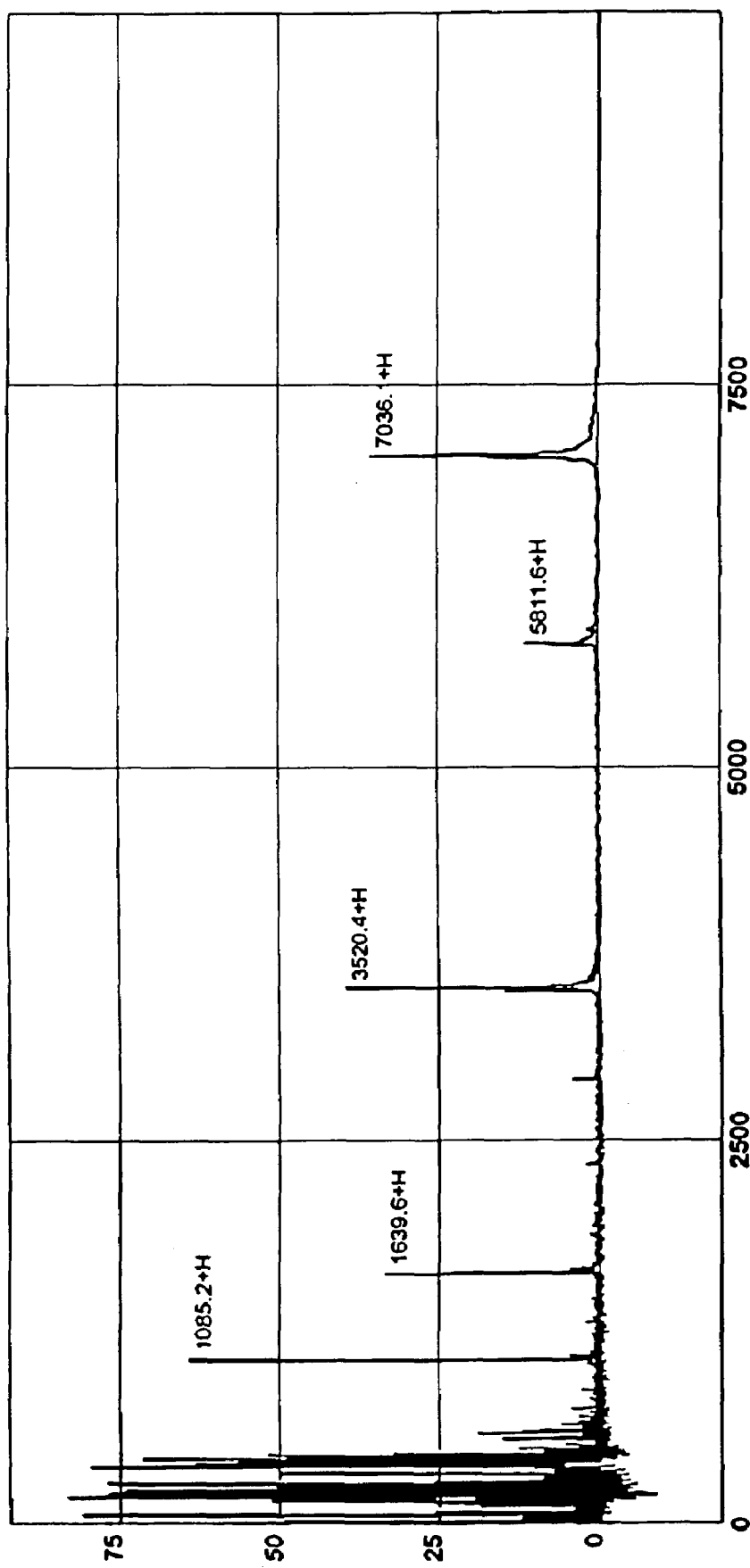
FIG. 11 is a mass spectrum of a peptide mixture, which was acquired using a linear copolymer of α-cyano-4-methacryloyloxycinnamic acid and styrene.
Figure 12:
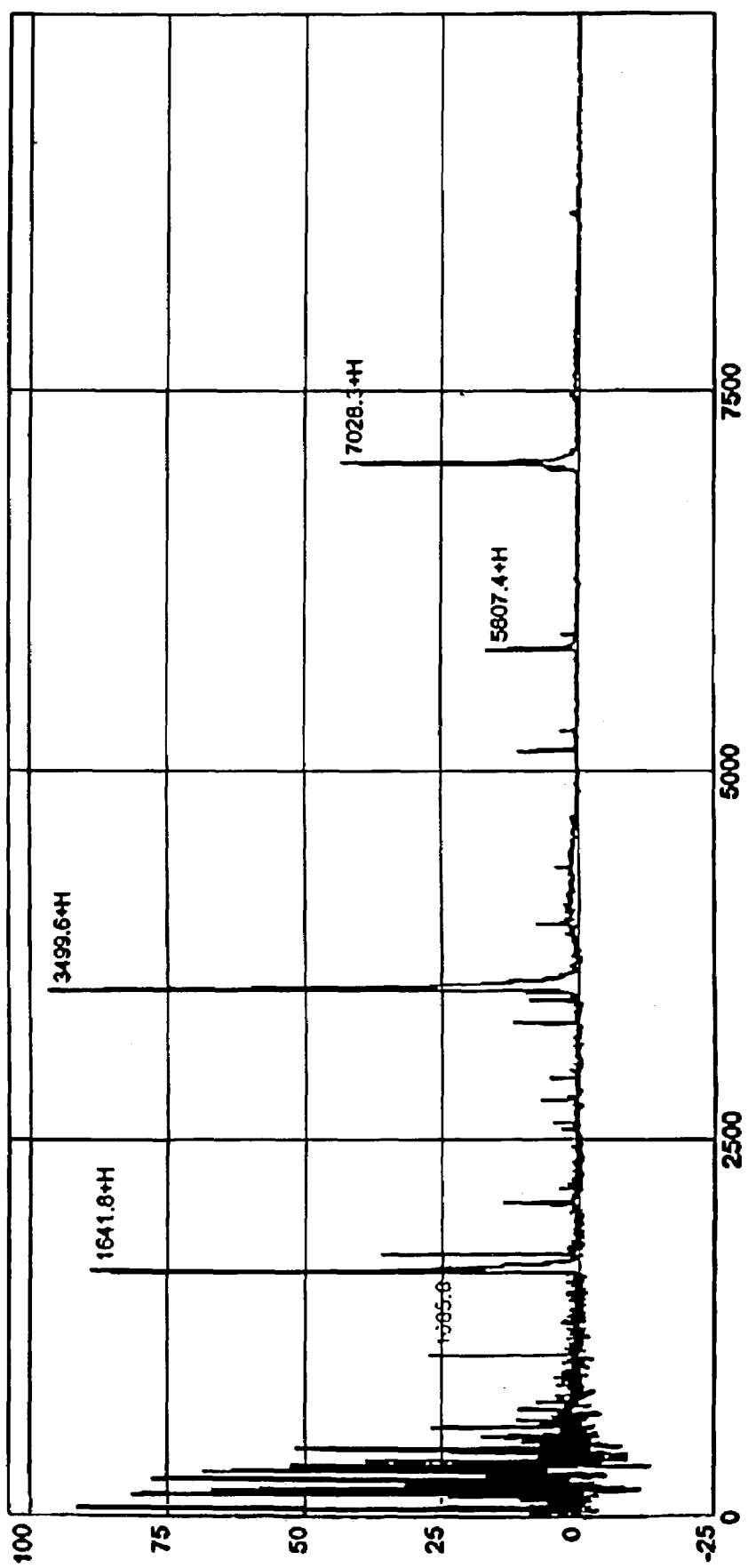
FIG. 12 is a mass spectrum of a peptide mixture, which was acquired using a copolymer of 2, 5-dimethacryloyoxy benzoic acid and acrylic acid.

The efficacy of the polymers of the invention in an analysis can be assessed by applying a standard or known sample, e.g., peptide, nucleic acid, to the chip incorporating a polymer of the invention and performing the desired analysis. In an exemplary embodiment, a standard peptide solution is applied to the chip and a desorption/ionization analysis is performed. For example mass spectra of a peptide were obtained using DHBMA (FIG. 4), DHAPheMA (FIG. 5), crosslinked CHCAMA (FIG. 6), poly-DEGDMA-CHCAMA (FIG. 7), copolymeric poly-CHCAMA/DHBMA (FIG. 8), copolymeric 2,5-dimethacryloyloxy benzoic acid and acrylic acid (FIG. 11) and poly-2,6-dimethacryloyloxy-acetophenone (FIG. 12).

Figure 9:
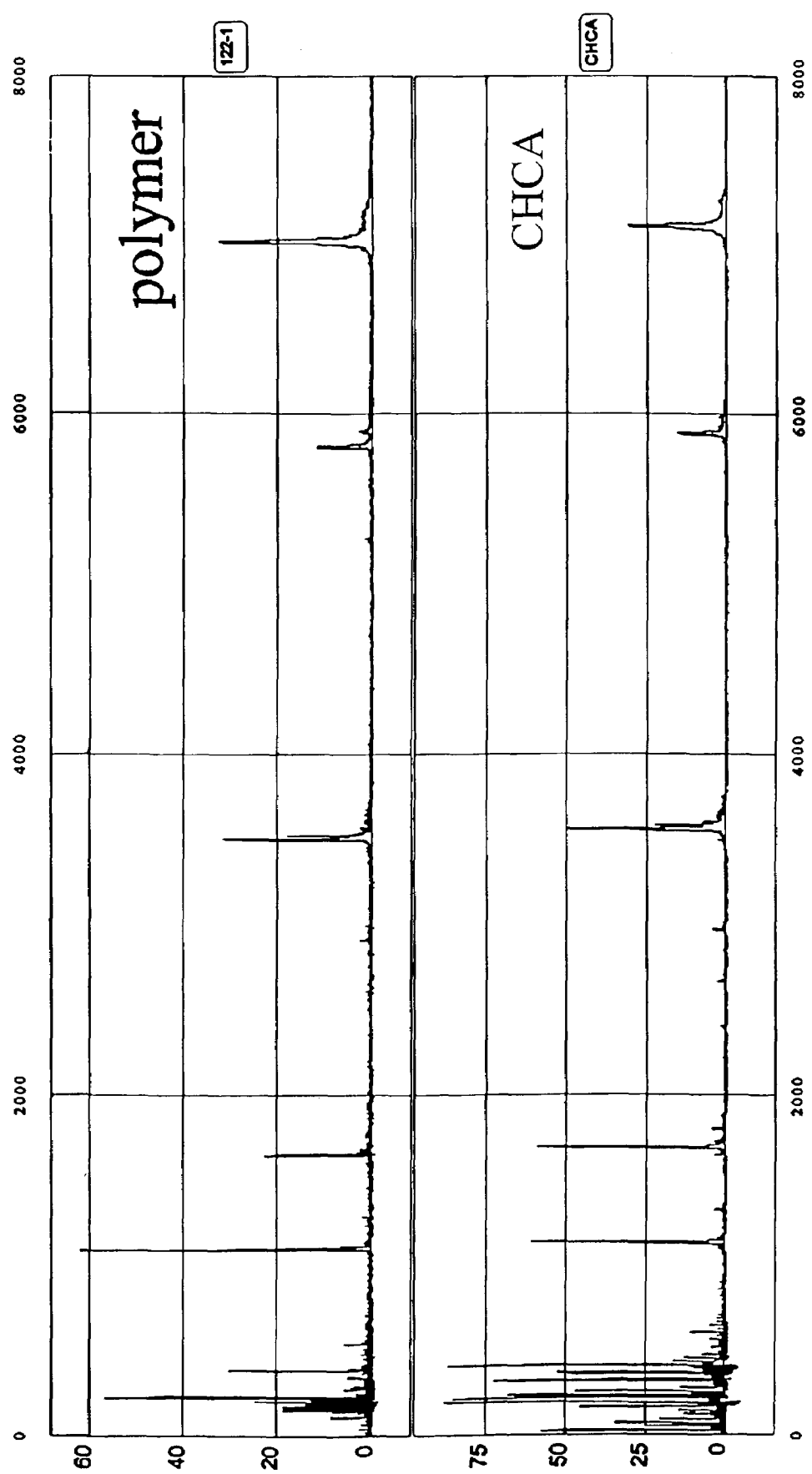
FIG. 9 is a comparison of a full mass range mass spectrum of a peptide mixture obtained using (A) an energy absorbing polymer (poly-CHCAMA) of the invention; and (B) standard MALDI using CHCA as the matrix.
Figure 10:
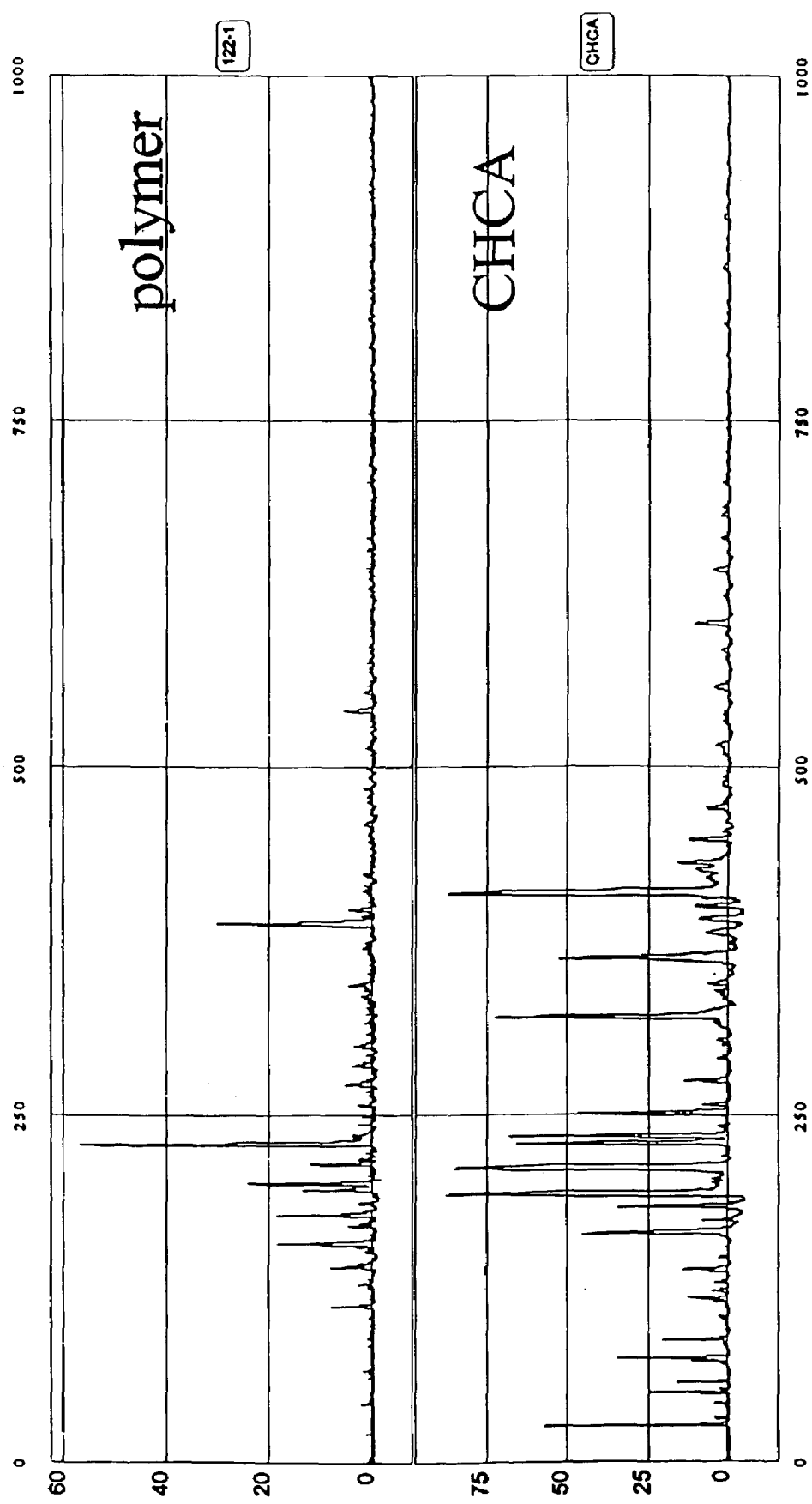
FIG. 10 is a low mass region of interest of the mass spectra of FIG. 9.

Surprisingly, use of the polymers of the invention in conjunction with a desorption/ionization mass spectrometric analysis produces results that are superior to those achieved using the small molecular matrix compositions recognized in the art. For example, an analysis of a standard peptide solution using a chip incorporating a polymer of the invention provides a mass spectrum with a lower level of background (FIG. 9), particularly in the low mass region of the spectrum (FIG. 10).

The above scheme is offered to exemplify the general concept of preparing the polymeric Surface Enhanced for Neat Desorption (SEND) compounds of the invention. Those of skill will appreciate that the polymeric compounds of the invention can be formed by any art-recognized method for polymerizing or copolymerizing monomers. The polymerization process can be accomplished using a number of possible synthetic routes including, but not limited to, homogeneous or heterogeneous chain-growth polymerization including a free radical or ionic polymerization reaction and photopolymerization with a photoinitiator, and step-growth polymerization, including addition-elimination reactions, addition-substitution reactions, nucleophilic substitution reactions, multiple-bond addition reactions, etc. The compositions of the invention can be prepared using bulk polymerization, solution polymerization, emulsion polymerization, suspension polymerization, condensation polymerization, etc. Suitable monomers are dependent upon the type of polymerization being utilized, and it is within the abilities of one of skill in the art to select the proper monomer and polymerization conditions to achieve a desired property or result.

After synthesis, the monomers and/or completed polymer can be further elaborated by a variety of chemical reactions well known to those skilled in the art. For example, in order to produce a matrix with anion exchange properties, the monomer can be co-polymerized with monomer having primary, secondary, tertiary, quaternary amine or chloromethyl group which can be aminated and quaternized. Production of an analogous SEND compound, containing cation exchange sites can be accomplished by a number of well-known synthetic schemes. By the same token, the monomer can be co-polymerized with monomers having sulfonic acid or carboxylic acid groups to have anionic compounds. Another distinctive method of preparing ionic SEND compounds is that the monomers synthesized according to the present invention can be copolymerized with styrene monomer and the copolymer can be further aminated through chloromethylation or sulfonation or carboxylation to have ionic SEND compounds. Also, a further representative method relies on the use of a dimethyl sulfide displacement reaction, in which a vinylbenzyl chloride-containing matrix component is first reacted with a solution of dimethyl sulfide. The resulting reaction product is a sulfonium based anion exchange compound. A second cation exchange site generation reagent is then added to the reaction mixture, which can be heated in order to help drive the reaction to completion. An exemplary reagent for this purpose is mercaptopropionic acid. A solution of this acid is first pH adjusted to about 11 and then mixed with the above suspension of sulfonium based anion exchange matrix. After heating the suspension at about 70° C. for a predetermined period of time, the substitution reaction is complete and the resulting adsorbent film component is now a weak acid cation exchange matrix.

Similar reaction pathways are available for preparing SEND compounds and SEND components with other binding functionalities. It is within the abilities of one of skill in the art to determine an appropriate reaction pathway to conjugate a selected binding functionality to the SEND compounds or SEND components (see, for example, Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

The Chip

Also provided by the instant invention are analytical devices that incorporate the SEND compound of the invention. The present invention contemplates a range of analytical devices that incorporate the SEND compound of the invention. The use of the SEND compound in an analytical device is exemplified herein by reference to a chip, which is of use as a substrate or probe component in desorption/ionization mass spectrometric methods of analysis. The focus of the following discussion on the chip format and its use in mass spectrometric analyses is for clarity of illustration alone and is not intended to limit the scope of the invention.

Thus, in one aspect, the present invention provides a device that includes a substrate having a surface, and a polymeric material attached to the surface. The polymeric material is adapted to receive analyte molecules, and it includes a photo-reactive polymer. The photo-reactive polymer absorbs photo-irradiation from a high fluence source to generate thermal energy, and transfers the thermal energy to the analyte, promoting its desorption and ionization.

The SEND compound of the invention is generally anchored to the surface of the chip substrate. The interaction between the SEND compound and the surface, which anchors the SEND compound to the surface can be a covalent, electrostatic, ionic, hydrogen bonding, hydrophobic-hydrophobic, or hydrophilic-hydrophilic interaction. When the interaction is non-covalent, it is referred to herein as "physical adhesion."

The Substrate

In the chip of the invention, the SEND compound is immobilized on a substrate, either directly or through linker arms that are intercalated between the substrate and the SEND compound. The SEND compound is immobilized on the plane of the substrate surface, or it is bound to a feature of the substrate surface, which may be flush with the surface, raised (e.g., island) or depressed (e.g., a well, trough, etc.). Substrates that are useful in practicing the present invention can be made of any stable material, or combination of materials. Moreover, useful substrates can be configured to have any convenient geometry or combination of structural features. The substrates can be either rigid or flexible and can be either optically transparent or optically opaque. The substrates can also be electrical insulators, conductors or semiconductors. When the sample to be applied to the chip is water based, the substrate preferable is water insoluble.

The materials forming the substrate are utilized in a variety of physical forms such as films, supported powders, glasses, crystals and the like. For example, a substrate can consist of a single inorganic oxide or a composite of more than one inorganic oxide. When more than one component is used to form a substrate, the components can be assembled in, for example a layered structure (i.e., a second oxide deposited on a first oxide) or two or more components can be arranged in a contiguous non-layered structure. Further the substrates can be substantially impermeable to liquids, vapors and/or gases or, alternatively, the substrates can be permeable to one or more of these classes of materials. Moreover, one or more components can be admixed as particles of various sizes and deposited on a support, such as a glass, quartz or metal sheet. Further, a layer of one or more components can be intercalated between two other substrate layers (e.g., metal-oxide-metal, metal-oxide-crystal). Those of skill in the art are able to select an appropriately configured substrate, manufactured from an appropriate material for a particular application.

Exemplary substrate materials include, but are not limited to, inorganic crystals, inorganic glasses, inorganic oxides, metals, organic polymers and combinations thereof. Inorganic glasses and crystals of use in the substrate include, but are not limited to, LiF, NaF, NaCl, KBr, KI, $CaF_2$, $MgF_2$, $HgF_2$, BN, $AsS_3$, ZnS, $Si_3N_4$, AlN and the like. The crystals and glasses can be prepared by art standard techniques. See, for example, Goodman, CRYSTAL GROWTH THEORY AND TECHNIQUES, Plenum Press, New York 1974. Alternatively, the crystals can be purchased commercially (e.g., Fischer Scientific). Inorganic oxides of use in the present invention include, but are not limited to, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $Sn)_2$, $PbO_2$ and the like. Metals of use in the substrates of the invention include, but are not limited to, gold, silver, platinum, palladium, nickel, copper and alloys and composites of these metals.

Metals are also of use as substrates in the present invention. The metal can be used as a crystal, a sheet or a powder. In those embodiments in which the metal is layered with another substrate component, the metal can be deposited onto the other substrate by any method known to those of skill in the art including, but not limited to, evaporative deposition, sputtering and electroless deposition.

The metal layers can be either permeable or impermeable to materials such as liquids, solutions, vapors and gases. Presently preferred metals include, but are not limited to, gold, silver, platinum, palladium, nickel, aluminum, copper, stainless steel, and other iron alloys.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins.

In a preferred embodiment, the substrate material is substantially non-reactive with the analyte, thus preventing non-specific binding between the substrate and the analyte or other components of an assay mixture. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

In a further preferred embodiment, the substrate material is substantially non-fluorescent or emits light of a wavelength range that does not interfere with the detection of the analyte. Exemplary low-background substrates include those disclosed by Cassin et al., U.S. Pat. No. 5,910,287 and Pham et al., U.S. Pat. No. 6,063,338.

The surface of a substrate of use in practicing the present invention can be smooth, rough and/or patterned. The surface can be engineered by the use of mechanical and/or chemical techniques. For example, the surface can be roughened or patterned by rubbing, etching, grooving, stretching, and the oblique deposition of metal films. The substrate can be patterned using techniques such as photolithography (Kleinfield et al., *J. Neurosci.* 8: 4098-120 (1998)), photoetching, chemical etching and microcontact printing (Kumar et al, *Langmuir* 10: 1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274-75 (1995). Similarly, using photolithography, patterns with features as small as 1 µm have been produced. See, Hickman et al., *J. Vac. Sci. Technol.* 12:607-16 (1994). Patterns that are useful in the present invention include those which comprise features such as wells, enclosures, partitions, recesses, inlets, outlets, channels, troughs, diffraction gratings and the like.

In an exemplary embodiment, the patterning is used to produce a substrate having a plurality of adjacent addressable features, wherein each of the features is separately identifiable by a detection means. In another exemplary embodiment, an addressable feature does not fluidically communicate with other adjacent features. Thus, an analyte, or other substance, placed in a particular feature remains substantially confined to that feature. In another preferred embodiment, the patterning allows the creation of channels through the device whereby fluids can enter and/or exit the device.

In those embodiments in which the SEND compound, the linker arm or a combination thereof are printed onto the substrate, the pattern can be printed directly onto the substrate or, alternatively, a "lift off" technique can be utilized. In the lift off technique, a patterned resist is laid onto the substrate, component of the chip is laid down in those areas not covered by the resist and the resist is subsequently removed: resists are known to those of skill in the art. See, for example, Kleinfield et al., *J. Neurosci.* 8:4098-120 (1998). In some embodiments, following removal of the resist, a second chip component, having a structure different from the first component layer is printed onto the substrate on those areas initially covered by the resist; a process that can be repeated any selected number of times with different components to produce a chip having a desired format.

Using the technique set forth above, substrates with patterns having regions of different chemical characteristics can be produced. Thus, for example, a pattern having an array of adjacent isolated features is created by varying the hydrophobicity/hydrophilicity, charge or other chemical characteristics of the pattern constituents. For example, hydrophilic compounds can be confined to individual hydrophilic features by patterning "walls" between the adjacent features using hydrophobic materials. Similarly, positively or negatively charged compounds can be confined to features having "walls" made of compounds with charges similar to those of the confined compounds. Similar substrate configurations are also accessible through microprinting a layer with the desired characteristics directly onto the substrate. See, Mrkish, M.; Whitesides, G. M., *Ann. Rev. Biophys. Biomol. Struct.* 25:55-78 (1996).

The specificity and multiplexing capacity of the chips of the invention can be increased by incorporating spatial encoding (e.g., spotted microarrays) into the chip substrate. Spatial encoding can be introduced into each of the chips of the invention. In an exemplary embodiment, binding functionalities for different analytes can be arrayed across the chip surface, allowing specific data codes (e.g., analyte-binding functionality specificity) to be reused in each location. In this case, the array location is an additional encoding parameter, allowing the detection of a virtually unlimited number of different analytes.

In the embodiments of the invention in which spatial encoding is utilized, they preferably utilize a spatially encoded array comprising m binding functionalities distributed over m regions of the substrate. Each of the m binding functionalities can be a different functionality or the same functionality, or different functionalities can be arranged in patterns on the surface. For example, in the case of SEND compound array of addressable locations, all the locations in a single row or column can have the same binding functionality. The m binding functionalities are preferably patterned on the substrate in a manner that allows the identity of each of the m locations to be ascertained. In a preferred embodiment, the m binding functionalities are ordered in a p by q SEND compound of (p×q) discrete locations, wherein each of the (p×q) locations has bound thereto at least one of the m binding functionalities. The microarray can be patterned from essentially any type of binding functionality.

The spatially encoded assay substrates can include essentially any number of compounds. In an embodiment in which the binding functionalities are polynucleotides (oligonucleotides or nucleic acids) or polypeptides, m is a number from 1 to 100, more preferably, from 10 to 1,000, and more preferably from 100 to 10,000.

In a particularly preferred embodiment, the substrate includes an aluminum support that is coated with a layer of silicon dioxide. In yet a further preferred embodiment, the silicon dioxide layer is from about 1000-3000 A in thickness. The silicon dioxide can provide —OH reactive groups that can function to couple or anchor a polymer to the surface of the chip.

Those of skill in the art will appreciate that the above-described and other methods are useful for preparing arrays of a wide variety of compounds in addition to nucleic acids, are useful for preparing arrays of a wide variety of compounds in addition to nucleic acids.

Analytes

The device and methods of the present invention can be used to detect any analyte, or class of analytes, which interact with a binding functionality in a detectable manner. The interaction between the analyte and binding functionality can be any physicochemical interaction, including covalent bonding, ionic bonding, hydrogen bonding, van der Waals interactions, attractive electronic interactions and hydrophobic/hydrophilic interactions.

In an exemplary embodiment, the interaction is an ionic interaction. In this embodiment, an acid, base, metal ion or metal ion-binding ligand is the analyte. In a further exemplary embodiment, the interaction is a hydrogen bonding interaction.

In a preferred embodiment, the analyte molecule is a biomolecule such as a polypeptide (e.g., peptide or protein), a polynucleotide (e.g., oligonucleotide or nucleic acid), a carbohydrate (e.g., simple or complex carbohydrate) or a lipid (e.g., fatty acid or polyglycerides, phospholipids, etc.). In the case of proteins, the nature of the analyte can depend upon the nature of the binding functionality. For example, one can capture a ligand using a receptor for the ligand as a binding functionality; an antigen using an antibody against the antigen, or a substrate using an enzyme that acts on the substrate.

The analyte can be derived from any sort of biological source, including body fluids such as blood, serum, saliva, urine, seminal fluid, seminal plasma, lymph, and the like. It also includes extracts from biological samples, such as cell lysates, cell culture media, or the like. For example, cell lysate samples are optionally derived from, e.g., primary tissue or cells, cultured tissue or cells, normal tissue or cells, diseased tissue or cells, benign tissue or cells, cancerous tissue or cells, salivary glandular tissue or cells, intestinal tissue or cells, neural tissue or cells, renal tissue or cells, lymphatic tissue or cells, bladder tissue or cells, prostatic tissue or cells, urogenital tissues or cells, tumoral tissue or cells, tumoral neovasculature tissue or cells, or the like.

In another embodiment, the analyte is a member selected from the group consisting of acids, bases, organic ions, inorganic ions, pharmaceuticals, herbicides, pesticides, and noxious gases. Each of these analytes can be detected as a vapor or a liquid. The analyte can be present as a component in a mixture of structurally unrelated compounds, an assay mixture, racemic mixtures of stereoisomers, non-racemic mixtures of stereoisomers, mixtures of diastereomers, mixtures of positional isomers or as a pure compound. Within the scope of the invention is method to detect a particular analyte of interest without interference from other substances within a mixture.

The analyte can be labeled with a fluorophore or other detectable group either directly or indirectly through interacting with a second species to which a detectable group is bound. When a second labeled species is used as an indirect labeling agent, it is selected from any species that is known to interact with the analyte species. Preferred second labeled species include, but are not limited to, antibodies, aptazymes, aptamers, streptavidin, and biotin.

The analyte can be labeled either before or after it interacts with the binding functionality. The analyte molecule can be labeled with a detectable group or more than one detectable group. Where the analyte species is multiply labeled with more than one detectable group, the groups are preferably distinguishable from each other.

Organic ions, that are substantially non-acidic and non-basic (e.g., quaternary alkylammonium salts) can be detected by a binding functionality. For example, a binding functionality with ion exchange properties is useful in the present invention. A specific example is the exchange of a cation such as dodecyltrimethylammonium cation for a metal ion such as sodium, using a spacer arm presenting a negatively charged species. Binding functionalities that form inclusion complexes with organic cations are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the device and method of the invention. Metal ions can be detected, for example, by their complexation or chelation by agents bound to the adsorbent layer. In this embodiment, the binding functionality can be a simple complexing moiety (e.g., carboxylate, amine, thiol) or can be a more structurally complicated agent (e.g., ethylenediaminepentaacetic acid, crown ethers, aza crowns, thia crowns).

Complex inorganic ions can be detected by, for example, their ability to compete with ligands for bound metal ions in ligand-metal complexes. When a ligand bound to a spacer arm or a substrate forms a metal-complex having a thermodynamic stability constant, which is less than that of the complex between the metal and the complex ion, the complex ion will replace the metal ion on the immobilized ligand. Methods of determining stability constants for compounds formed between metal ions and ligands are well known to those of skill in the art. Using these stability constants, substrates including affinity moieties that are specific for particular ions can be manufactured. See, Martell, A. E., Motekaitis, R. J., DETERMINATION AND USE OF STABILITY CONSTANTS, 2d Ed., VCH Publishers, New York 1992.

Small molecules such as pesticides, herbicides, and the like can be detected by the use of a number of different binding functionality motifs. Acidic or basic components can be detected as described above. An analyte's metal binding capability can also be used to advantage, as described above for complex ions. Additionally, if these analytes bind to an identified biological structure (e.g., a receptor), the receptor can be immobilized on the substrate, a spacer arm. Techniques are also available in the art for raising antibodies that are highly specific for a particular species. Thus, it is within the scope of the present invention to make use of antibodies against small molecules, pesticides, agents of war and the like for detection of those species. Techniques for raising antibodies to herbicides and pesticides are known to those of skill in the art. See, Harlow, Lane, MONOCLONAL ANTIBODIES: A LABORATORY MANUAL, Cold Springs Harbor Laboratory, Long Island, N.Y., 1988.

In another exemplary embodiment, the analyte is detected by binding to an immobilized binding functionality is an organophosphorous compound such as an insecticide.

Method of Making the Chip

In another aspect, the present invention provides methods of making a SEND compound and a chip of the invention. As discussed above, the SEND compound may be formed from substantially any appropriate EAM or combination of EAMs. Moreover, the SEND compound may be a homopolymer, or a copolymer. Cross-linked polymers are also useful as SEND compounds of the invention.

The method of forming a chip of the invention includes depositing onto a substrate a polymer that includes an EAM having analyte-receiving properties and energy absorption properties as set forth above. The polymer can be formed in situ on the chip or prior to its deposition onto the chip.

Thus, in an exemplary embodiment, the invention provides a method of making a device for use in conjunction with a laser desorption analysis of an analyte molecule. The method includes contacting a surface of a substrate with a polymeric precursor comprising a first polymerizable monomeric precursor of a photo-reactive polymer; and polymerizing the monomeric precursor, thereby forming the layer of photo-reactive polymer. The SEND compound is generally attached to the substrate via a chemical or physical interaction.

In an exemplary embodiment of the method set forth above, the polymeric precursor further includes a second polymerizable monomeric precursor of the photo-reactive polymer. The structure of the second polymerizable monomeric precursor is different from that of the first. For example, the second monomeric precursor can be selected from a polymerizable monomeric photo-reactive species, a polymerizable analyte-binding species, a polymerizable cross-linking species and a combination thereof.

In another exemplary embodiment, the invention provides another method of making a chip of the invention. The method includes contacting a surface of a substrate with a photo-reactive polymer comprising a first polymeric photo-reactive species. Similar to the method set forth above, the method also generally includes the attachment of the polymer to the substrate via a chemical or physical interaction.

In a still further exemplary embodiment, the chip of the invention is washed after the polymeric matrix of the invention is deposited onto the substrate surface. The washing process is practiced with a solvent such as water or an organic solvent, e.g., alcohol, ether, ester, DMF, halocarbon (e.g., $CH_2Cl_2$, $HCCl_3$, $CCl_4$), amide, etc. The washing process is useful, for example, to remove reagents, reactants and small or incompletely polymerized species from the chip, or to cause the polymeric matrix to swell or contract. In contrast, the matrices used in MALDI and SELDI are removed from the chip by such a washing process, thereby eliminating the beneficial effects of the matrix to the analysis.

In the method set forth above, the photo-reactive polymer optionally includes a second polymeric species, having a structure different from the first polymeric photo-reactive precursor. For example, the second polymeric species can be selected from a second polymeric photo-reactive species, a polymeric analyte binding species, a polymeric cross-linking species and a combination thereof.

Assays

The chip of the present invention is useful in performing assays of substantially any format including, but not limited to chromatographic capture, immunoassays, competitive assays, DNA or RNA binding assays, fluorescence in situ hybridization (FISH), protein and nucleic acid profiling assays, sandwich assays and the like.

Thus, in a further aspect, the present invention provides a method of detecting or analyzing a sample. The method includes desorbing and ionizing the sample from a chip that includes a polymeric SEND compound of the invention. The SEND compound includes an EAM. The SEND compound is a discrete polymer that is either formed prior to its deposition onto the chip or, alternatively, is formed in situ on the chip. Alternatively, a polymeric material of this invention, in particular a linear polymer, can be contacted with a molecular analyte (e.g., mixed) and placed on the surface of a mass spectrometry probe without chemical binding for subsequent detection. In certain embodiment, the polymeric material of this invention can replace the traditional matrix material used in the performance of MALDI, with improved detection especially at the low molecular weight ranges. In other embodiments, the polymeric material includes a binding functionality for. the practice of SELDI (surface-enhanced laser desorption/ionization) mass spectrometry. (See, e.g., U.S. Pat. No. 5,719,060 (Hutchens and Yip)).

The following discussion focuses on the use of the methods of the invention in practicing exemplary assays. This focus is for clarity of illustration only and is not intended to define or limit the scope of the invention. Those of skill in the art will appreciate that the method of the invention is broadly applicable to any assay technique for detecting the presence and/or amount of a target.

The chip of the present invention is useful for performing retentate chromatography. Retentate chromatography has many uses in biology and medicine. These uses include combinatorial biochemical separation and purification of analytes, protein profiling of biological samples, the study of differential protein expression and molecular recognition events, diagnostics and drug discovery. Retentate chromatography is described in Hutchens and Yip, U.S. Pat. No. 6,225,047.

One basic use of retentate chromatography as an analytical tool involves exposing a sample to a combinatorial assortment of different adsorbent/eluant combinations and detecting the behavior of the analyte under the different conditions. This both purifies the analyte and identifies conditions useful for detecting the analyte in a sample. Substrates having adsorbents identified in this way can be used as specific detectors of the analyte or analytes. In a progressive extraction method, a sample is exposed to a first adsorbent/eluant combination and the wash, depleted of analytes that are adsorbed by the first adsorbent, is exposed to a second adsorbent to deplete it of other analytes. Selectivity conditions identified to retain analytes also can be used in preparative purification procedures in which an impure sample containing an analyte is exposed, sequentially, to adsorbents that retain it, impurities are removed, and the retained analyte is collected from the adsorbent for a subsequent round. See, for example, U.S. Pat. No. 6,225,047.

The chip of the invention is useful in applications such as sequential extraction of analytes from a solution, progressive resolution of analytes in a sample, preparative purification of an analyte, making probes for specific detection of analytes, methods for identifying proteins, methods for assembling multimeric molecules, methods for performing enzyme assays, methods for identifying analytes that are differentially expressed between biological sources, methods for identifying ligands for a receptor, methods for drug discovery (e.g., screening assays), and methods for generating agents that specifically bind an analyte.

In other applications, chip-based assays based on specific binding reactions are useful to detect a wide variety of targets such as drugs, hormones, enzymes, proteins, antibodies, and infectious agents in various biological fluids and tissue samples. In general, the assays consist of a target, a binding functionality for the target, and a means of detecting the target after its immobilization by the binding functionality (e.g., a detectable label). Immunological assays involve reactions between immunoglobulins (antibodies), which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

The present invention provides a chip useful for performing assays that are useful for confirming the presence or absence of a target in a sample and for quantitating a target in a sample. An exemplary assay format with which the invention can be used is an immunoassay, e.g., competitive assays, and sandwich assays. The invention is further illustrated using these two assay formats. The focus of the following discussion on competitive assays and sandwich assays is for clarity of illustration and is not intended to either define or limit the scope of the invention. Those of skill in the art will appreciate that the invention described herein can be practiced in conjunction with a number of other assay formats.

In an exemplary competitive binding assay, two species, one of which is the target, compete for a binding functionality on an adsorbent film. After an incubation period, unbound materials are washed off and the amount of target, or other species bound to the functionality is compared to reference amounts for determination of the target, or other species concentration in the assay mixture. Other competitive assay motifs using labeled target and/or labeled binding functionality and/or labeled reagents will be apparent to those of skill in the art.

A second type of assay is known as a sandwich assay and generally involves contacting an assay mixture with a surface having immobilized thereon a first binding functionality immunologically specific for that target. A second solution comprising a detectable binding material is then added to the assay. The labeled binding material will bind to a target, which is bound to the binding functionality. The assay system is then subjected to a wash step to remove labeled binding material, which failed to bind with the target and the amount of detectable material remaining on the chip is ordinarily proportional to the amount of bound target. In representative assays one or more of the target, binding functionality or binding material is labeled with a fluorescent label.

In addition to detecting an interaction between a binding functionality and a target, it is frequently desired to quantitate the magnitude of the affinity between two or more binding partners. The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. One of the three binding partners (i.e., the ligand, antagonist or receptor) is bound to the binding functionality, or is the binding functionality. In an exemplary embodiment, the receptor is bound to the adsorbent film. Various concentrations of ligand are added to different chip regions. A detectable antagonist is then applied to each region to a chosen final concentration. The treated chip will generally be incubated at room temperature for a preselected time. The receptor-bound antagonist can be separated from the unbound antagonist by filtration, washing or a combination of these techniques. Bound antagonist remaining on the chip can be measured as discussed herein. A number of variations on this general experimental procedure will be apparent to those of skill in the art.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: Ki=IC50/(1+L/Kd), where L is the concentration of the ligand used in the competitive binding assay, and Kd is the dissociation constant of the ligand as determined by Scatchard analysis. These assays are described, among other places, in Maddox et al., *J Exp Med.*, 158: 1211 (1983); Hampton et al., SEROLOGICAL METHODS, A LABORATORY MANUAL, APS Press, St. Paul, Minn., 1990.

The chip and method of the present invention are also of use in screening libraries of compounds, such as combinatorial libraries. The synthesis and screening of chemical libraries to identify compounds, which have novel bioactivities, and material science properties is now a common practice. Libraries that have been synthesized include, for example, collections of oligonucleotides, oligopeptides, and small and large molecular weight organic or inorganic molecules. See, Moran et al., PCT Publication WO 97/35198, published Sep. 25, 1997; Baindur et al., PCT Publication WO 96/40732, published Dec. 19, 1996; Gallop et al., *J. Med. Chem.* 37:1233-51 (1994).

Virtually any type of compound library can be probed using the method of the invention, including peptides, nucleic acids, saccharides, small and large molecular weight organic and inorganic compounds. In a presently preferred embodiment, the libraries synthesized comprise more than 10 unique compounds, preferably more than 100 unique compounds and more preferably more than 1000 unique compounds.

The nature of these libraries is better understood by reference to peptide-based combinatorial libraries as an example. The present invention is useful for assembling peptide-based combinatorial libraries, but it is not limited to these libraries. The methods of the invention can be used to screen libraries of essentially any molecular format, including small organic molecules, carbohydrates, nucleic acids, polymers, organometallic compounds and the like. Thus, the following discussion, while focusing on peptide libraries, is intended to be illustrative and not limiting.

Libraries of peptides and certain types of peptide mimetics, called "peptoids", are assembled and screened for a desirable biological activity by a range of methodologies (see, Gordon et al., *J. Med Chem.*, 37: 1385-1401 (1994); Geysen, (*Bioorg. Med. Chem. Letters*, 3: 397-404 (1993); *Proc. Natl. Acad. Sci. USA*, 81: 3998 (1984); Houghton, *Proc. Natl. Acad. Sci. USA*, 82: 5131 (1985); Eichler et al., *Biochemistry*, 32: 11035-11041 (1993); and U.S. Pat. No. 4,631,211); Fodor et al., *Science*, 251: 767 (1991); Huebner et al. (U.S. Pat. No. 5,182,366). Small organic molecules have also been prepared by combinatorial means. See, for example, Camps. et al., *Annaks de Quimica*, 70: 848 (1990); U.S. Pat. No. 5,288,514; U.S. Pat. No. 5,324,483; Chen et al., *J. Am. Chem. Soc.*, 116: 2661-2662 (1994).

In an exemplary embodiment, a binding domain of a receptor, for example, serves as the focal point for a drug discovery assay, where, for example, the receptor is immobilized, and incubated both with agents (i.e., ligands) known to interact with the binding domain thereof, and a quantity of a particular drug or inhibitory agent under test. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

In each of the assays set forth above, a washing step or steps is optionally incorporated. The washing step(s) can be performed before the chip is contacted with the analyte and/or after the chip is contacted with the analyte. In a still further exemplary embodiment, the chip of the invention is washed after the polymeric matrix of the invention is deposited onto the substrate surface. The washing process is practiced with a solvent such as water or an organic solvent, e.g., alcohol, ether, ester, DMF, halocarbon (e.g., $CH_2Cl_2$, $HCCl_3$, $CCl_4$), amide, etc. The choice of solvent is dependent on the polymer and the polymer and the analyte if the washing is performed subsequent to contacting the polymer with the analyte. The choice of the correct solvent for a particular application is well within the abilities of those of skill in the art. The washing process is useful, for example, to remove reagents, reactants and small or incompletely polymerized species from the chip, or to cause the polymeric matrix to swell or contract. Moreover, the washing process can be used to remove components of the assay mixture that interfere with the analysis, and which are amenable to removal from the chip under conditions that allow the desired analyte mixture component(s) to continue to interact with the chip. In contrast, the matrices currently used in MALDI and SELDI are removed from the chip by such a washing process, thereby eliminating the beneficial effects of the matrix to the analysis. Thus, a washing step after the deposition of the matrix on the chip cannot be practiced in either MALDI or SELDI methods.

Detection

The presence of the analyte interacting with the SEND compound can be detected by the use of microscopes, spectrometry, electrical techniques and the like. For example, in certain embodiments light in the visible region of the spectrum is used to illuminate details of the SEND compound (e.g., reflectance, transmittance, birefringence, diffraction, etc.). Alternatively, the light can be passed through the SEND compound and the amount of light transmitted, absorbed or reflected can be measured. The device can utilize a backlighting device such as that described in U.S. Pat. No. 5,739,879. Light in the ultraviolet and infrared regions is also of use in the present invention.

For the detection of low concentrations of analytes in the field of diagnostics, the methods of chemiluminescence and electrochemiluminescence are gaining wide spread acceptance. These methods of chemiluminescence and electrochemiluminescence provide a means to detect low concentrations of analytes by amplifying the number of luminescent molecules or photon generating events manyfold, the resulting "signal amplification" then allowing for detection of low concentration analytes.

In another embodiment, a fluorescent label is used to label one or more assay component or region of the chip. Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226-35 (1993)), and the like.

Microscopic techniques of use in practicing the invention include, but are not limited to, simple light microscopy, confocal microscopy, polarized light microscopy, atomic force microscopy (Hu et al., *Langmuir* 13:5114-5119 (1997)), scanning tunneling microscopy (Evoy et al., *J. Vac. Sci. Technol A* 15:1438-1441, Part 2 (1997)), and the like.

Spectroscopic techniques of use in practicing the present invention include, for example, infrared spectroscopy (Zhao et al., *Langmuir* 13:2359-2362 (1997)), raman spectroscopy (Zhu et al., *Chem. Phys. Lett.* 265:334-340 (1997)), X-ray photoelectron spectroscopy (Jiang et al., *Bioelectroch. Bioener.* 42:15-23 (1997)) and the like. Visible and ultraviolet spectroscopies are also of use in the present invention.

Of particular interest is the use of mass spectrometric techniques to detect analytes with the SEND compound, particularly those mass spectrometric methods utilizing desorption of the analyte from the SEND compound and direct detection of the desorbed analytes. In one embodiment, the method is SELDI, a mass spectrometric technique in which analytes are captured on the surface of a biochip and detected by, e.g., laser desorption/ionization mass spectrometry.

Desorbing the analyte from the SEND compound involves exposing the analyte to an appropriate energy source. Usually this means striking the analyte with radiant energy or energetic particles. For example, the energy can be light energy in the form of laser energy (e.g., UV laser) or energy from a flash lamp. Alternatively, the energy can be a stream of fast atoms. Heat may also be used to induce/aid desorption.

The desorbed analyte can be detected by any of several means. When the analyte is ionized in the process of desorption, such as in laser desorption/ionization mass spectrometry, the detector can be an ion detector. Mass spectrometers generally include means for determining the time-of-flight of desorbed ions. This information is converted to mass. One need not determine the mass of desorbed ions, however, to resolve and detect them: the fact that ionized analytes strike the detector at different times provides detection and resolution of them.

A plurality of detection means can be implemented in series to fully interrogate the analyte components and function associated with retentate at each location in the array.

Desorption detectors comprise means for desorbing the analyte from the adsorbent and means for directly detecting the desorbed analyte. That is, the desorption detector detects desorbed analyte without an intermediate step of capturing the analyte in another solid phase and subjecting it to subsequent analysis. Detection of an analyte normally will involve detection of signal strength. This, in turn, reflects the quantity of analyte adsorbed to the adsorbent.

The desorption detector also can include other elements, e.g., a means to accelerate the desorbed analyte toward the detector, and a means for determining the time-of-flight of the analyte from desorption to detection by the detector.

A preferred desorption detector is a laser desorption/ionization mass spectrometer, which is well known in the art. The mass spectrometer includes a port into which the substrate that carries the adsorbed analytes, e.g., a probe, is inserted. Striking the analyte with energy, such as laser energy desorbs the analyte. Striking the analyte with the laser results in desorption of the intact analyte into the flight tube and its ionization. The flight tube generally defines a vacuum space. Electrified plates in a portion of the vacuum tube create an electrical potential which accelerate the ionized analyte toward the detector. A clock measures the time of flight and the system electronics determines velocity of the analyte and converts this to mass. As any person skilled in the art understands, any of these elements can be combined with other elements described herein in the assembly of desorption detectors that employ various means of desorption, acceleration, detection, measurement of time, etc. An exemplary detector further includes a means for translating the surface so that any spot on the array is brought into line with the laser beam.

Informatics

As high-resolution, high-sensitivity datasets acquired using the methods of the invention become available to the art, significant progress in the areas of diagnostics, therapeutics, drug development, biosensor development, and other related areas will occur. For example, disease markers can be identified and utilized for better confirmation of a disease condition or stage (see, U.S. Pat. Nos. 5, 672,480; 5,599,677; 5,939,533; and 5,710,007). Subcellular toxicological information can be generated to better direct drug structure and activity correlation (see, Anderson, L., "Pharmaceutical Proteomics: Targets, Mechanism, and Function," paper presented at the IBC Proteomics conference, Coronado, Calif. (Jun. 11-12, 1998)). Subcellular toxicological information can also be utilized in a biological sensor device to predict the likely toxicological effect of chemical exposures and likely tolerable exposure thresholds (see, U.S. Pat. No. 5,811,231). Similar advantages accrue from datasets relevant to other biomolecules and bioactive agents (e.g., nucleic acids, saccharides, lipids, drugs, and the like).

Thus, in another preferred embodiment, the present invention provides a database that includes at least one set of data assay data. The data contained in the database is acquired using a method of the invention and/or a QD-labeled species of the invention either singly or in a library format. The database can be in substantially any form in which data can be maintained and transmitted, but is preferably an electronic database. The electronic database of the invention can be maintained on any electronic device allowing for the storage of and access to the database, such as a personal computer, but is preferably distributed on a wide area network, such as the World Wide Web.

The focus of the present section on databases, which include peptide sequence specificity data is for clarity of illustration only. It will be apparent to those of skill in the art that similar databases can be assembled for any assay data acquired using an assay of the invention.

The compositions and methods described herein for identifying and/or quantitating the relative and/or absolute abundance of a variety of molecular and macromolecular species from a biological sample provide an abundance of information, which can be correlated with pathological conditions, predisposition to disease, drug testing, therapeutic monitoring, gene-disease causal linkages, identification of correlates of immunity and physiological status, among others. Although the data generated from the assays of the invention is suited for manual review and analysis, in a preferred embodiment, prior data processing using high-speed computers is utilized.

An array of methods for indexing and retrieving biomolecular information is known in the art. For example, U.S. Pat. Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multi-dimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

The present invention provides a computer database comprising a computer and software for storing in computer-retrievable form assay data records cross-tabulated, for example, with data specifying the source of the target-containing sample from which each sequence specificity record was obtained.

In an exemplary embodiment, at least one of the sources of target-containing sample is from a tissue sample known to be free of pathological disorders. In a variation, at least one of the sources is a known pathological tissue specimen, for example, a neoplastic lesion or a tissue specimen containing a pathogen such as a virus, bacteria or the like. In another variation, the assay records cross-tabulate one or more of the following parameters for each target species in a sample: (1) a unique identification code, which can include, for example, a target molecular structure and/or characteristic separation coordinate (e.g., electrophoretic coordinates); (2) sample source; and (3) absolute and/or relative quantity of the target species present in the sample.

The invention also provides for the storage and retrieval of a collection of target data in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the target data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 target data records cross-tabulated with target source.

When the target is a peptide or nucleic acid, the invention preferably provides a method for identifying related peptide or nucleic acid sequences, comprising performing a computerized comparison between a peptide or nucleic acid sequence assay record stored in or retrieved from a computer storage device or database and at least one other sequence. The comparison can include a sequence analysis or comparison algorithm or computer program embodiment thereof (e.g., FASTA, TFASTA, GAP, BESTFIT) and/or the comparison may be of the relative amount of a peptide or nucleic acid in a pool of sequences determined from a polypeptide or nucleic acid sample of a specimen.

The invention also preferably provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding data from an assay of the invention in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal tranmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The invention also provides a method for transmitting assay data that includes generating an electronic signal on an electronic communications device, such as a modem, ISDN terminal adapter, DSL, cable modem, ATM switch, or the like, wherein the signal includes (in native or encrypted format) a bit pattern encoding data from an assay or a database comprising a plurality of assay results obtained by the method of the invention.

In a preferred embodiment, the invention provides a computer system for comparing a query target to a database containing an array of data structures, such as an assay result obtained by the method of the invention, and ranking database targets based on the degree of identity and gap weight to the target data. A central processor is preferably initialized to load and execute the computer program for alignment and/or comparison of the assay results. Data for a query target is entered into the central processor via an I/O device. Execution of the computer program results in the central processor retrieving the assay data from the data file, which comprises a binary description of an assay result.

The target data or record and the computer program can be transferred to secondary memory, which is typically random access memory (e.g., DRAM, SRAM, SGRAM, or SDRAM). Targets are ranked according to the degree of correspondence between a selected assay characteristic (e.g., binding to a selected binding functionality) and the same characteristic of the query target and results are output via an I/O device. For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention also preferably provides the use of a computer system, such as that described above, which comprises: (1) a computer; (2) a stored bit pattern encoding a collection of peptide sequence specificity records obtained by the methods of the invention, which may be stored in the computer; (3) a comparison target, such as a query target; and (4) a program for alignment and comparison, typically with rank-ordering of comparison results on the basis of computed similarity values.

The materials, methods and devices of the present invention are further illustrated by the examples, which follow. These examples are offered to illustrate, but not to limit the claimed invention.

EXAMPLES

Materials and Methods

In the examples below, unless otherwise stated, temperatures are given in degrees Celsius (° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

The efficacy of the polymeric EAM of the invention was assessed using a buffered peptide mixture containing approximately 4 µM vasopressin, 2 µM somatostatin, 4 µM insulin B-chain, 7 µM h,r-insulin and 5 µM hirudin. Approximately 1-2 µL of the peptide mixture was deposited onto the chip at each spot having the polymer film as described below.

Example 1

Synthesis of α-cyano-4-methacryloyloxycinnamic acid

In a 100 mL three-necked glass reactor equipped with a magnetic stirrer, 3.2 g of α-cyano-4-hydroxycinnamic acid (from Sigma-Aldrich, Milwaukee, USA. Melting point: 242° C. recorded by IA6200) was added to a solution of 2.00 g of potassium hydroxide (Aldrich) in 35 g of water and 30 g of acetone (from VWR, West Chester, Pa.) and the reactor was placed in an ice bath. Methacryloyl chloride (from Aldrich), 2.2 mL, was placed separately in a dropping funnel and set onto the three-necked glass reactor. The methacryloyl chloride was added drop-wise into the reactor slowly. The reaction was continued in an ice bath for two hours.

The resulting reaction mixture was acidified with dilute aqueous hydrochloric acid. The precipitate was filtered off and dried in vacuo. The dried filter cake was dissolved in 10 mL of glacial acetic acid (from Aldrich) and cooled in a refrigerator overnight. The re-crystallized material was dried and dissolved in methanol (from Aldrich). The methanol solution was placed in a freezer overnight. The resulting crystals were filtered off and dried in vacuo. The yield was 0.9 g. Meting point was determined to be 190~192° C. by means of a Digital Melting Point Apparatus IA9200 (made by Electrothermal Engineering, Essex, UK). The NMR spectra showed the corresponding absorptions to α-cyano-4-methacryloyloxycinnamic acid.

Example 2

Synthesis of α-cyano-4-acryloyloxycinnamic Acid

In a 100 mL three-necked glass reactor equipped with a magnetic stirrer, 1.7 g of α-cyano-4-hydroxycinnamic acid (from Sigma-Aldrich, Milwaukee, Wis., Melting Point: 242° C. recorded by IA9200) was added to a solution of 2.00 g of potassium hydroxide (Aldrich) in 25 g of water and 4.5 g of acetone (from VWR, West Chester, Pa.) and the reactor was placed in an ice bath.

Acryloyl chloride (from Aldrich), 1.7 mL, was placed separately in a dropping funnel and set onto the three-necked glass reactor. The acryloyl chloride was added drop-wise into the reactor slowly. The reaction was continued in an ice bath for two hours.

The resulting reaction mixture was acidified with dilute aqueous hydrochloric acid. The precipitate was filtered off and dried in vacuo. The dried filter cake was dissolved in 9 mL of glacial acetic acid (from Aldrich) and cooled in a refrigerator over night. The re-crystallized resulting material was dried and dissolved in methanol (from Aldrich). The methanol solution was placed in a freezer overnight. The crystals were filtered off and dried in vacuo. The yield was 0.7 g. Melting point was determined to be 187-191° C. by means of a Digital Melting Point Apparatus IA9200 (made by Electrothermal Engineering, Essex, UK).

Example 3

Synthesis of 2,5-dimethacryloyloxy benzoic Acid

In a 100 mL three-necked glass reactor, 3.0 g of 2,5-dihydroxybenzoic acid (from Sigma-Aldrich, Milwaukee, USA, Melting point: 154° C. recorded by IA6200) was added to a solution of 6.2 g of potassium hydroxide (from Aldrich) in 12 mL of water and 12 g of acetone (from VWR, West Chester, Pa.) and the reactor was placed in an ice bath. Methacryloyl chloride (from Aldrich), 4.16 mL, was placed separately in a dropping funnel and was set onto the three-necked glass reactor. The methacryloyl chloride was added drop-wise into the reactor slowly. The reaction was continued in an ice bath for two hours.

The resulting reaction mixture was acidified with dilute aqueous hydrochloric acid. The precipitate was filtered off and dried in vacuo. The dried filter cake was dissolved in 10 mL of glacial acetic acid (from Aldrich) and cooled in a refrigerator overnight. The re-crystallized resulting material was filtered, dried and dissolved in methanol (from Aldrich). The methanol solution was placed in a freezer overnight. The crystals were filtered off and dried in vacuo. The yield was 0.8 g. Melting point was determined to be 140-141° C. by means of a Digital Melting Point Apparatus IA9200.

Example 4

Synthesis of 2,6-dimethacryloyloxy Acetophenone

In a 100 mL three-necked glass reactor, 1.5 g of 2,6-dihydroxyacetophenone (from Sigma-Aldrich, Milwaukee, USA Melting point: 125° C. recorded by IA6200) was added to a solution of 3.0 g of potassium hydroxide (from Aldrich) in 12 g of water and 12 g of acetone (from VWR) and the reactor was placed in an ice bath. Methacryloyl chloride (from Aldrich), 2.08 mL, was placed separately in a dropping funnel and set onto the three-necked glass reactor. The methacryloyl chloride was added slowly drop-wise into the reactor. The reaction was continued in an ice bath for two hours.

The resulting reaction mixture was acidified with a dilute aqueous hydrochloric acid. The precipitate was filtered off and dried in vacuo. The dried filter cake was dissolved in 10 mL of glacial acetic acid (from Aldrich) and cooled in a refrigerator overnight. The re-crystallized resulting material was filtered off, dried and dissolved in methanol (from Aldrich). The methanol solution was placed in a freezer overnight. The crystals were filtered off and dried in vacuo. The yield was 0.8 g. Melting point was 156-158° C.

Example 5

Synthesis of trans-3,5-dimethoxy-4-acryloyloxycinnamic Acid

In a 100 mL three-necked glass reactor, 2.0 g of trans-3,5-dimethoxy-4-hydroxycinnamic acid (Sinapinic acid from Sigma-Aldrich, Milwaukee, Wis.; melting point: 202° C. recorded by IA6200) was added to a solution of 3.0 g of potassium hydroxide (Aldrich) in 30 g of water and 5 mL of acetone (from VWR) and the reactor was placed in an ice bath. Acryloyl chloride (from Aldrich), 1.8 mL, was placed separately in a dropping funnel and was set onto the three-necked glass reactor. The acryloyl chloride was added slowly drop-wise into the reactor. The reaction was continued in an ice bath for two hours.

The resulting reaction mixture was acidified with dilute aqueous hydrochloric acid. The precipitate was filtered off and dried in vacuo. The dried filter cake was dissolved in 10 mL of glacial acetic acid (from Aldrich) and cooled in a refrigerator overnight. The re-crystallized material was filtered, dried and dissolved in methanol (from Aldrich). The methanol solution was placed in a freezer overnight. The resulting crystals were filtered and dried in vacuo. The yield was 0.6 g: melting point 178-180° C.

Example 6

Polymerization of Cross-Linked α-cyano-4-methacryloyloxycinnamic Acid

In a small glass bottle, 4.9 mg of α-cyano-4-methacryloyloxycinnamic acid prepared according to the method of Example 1 and 1 µL of polyethylene glycol dimethacrylate (MW~250 from Polyscience, Washington, Pa.) were dissolved in 10 mL propylene carbonate (Aldrich). To the above solution, 1 µL of 10% lauroyl peroxide (Aldrich) in methanol was added and mixed well. The small glass bottle with the monomer mixture was placed in an oven at 95° C. for 20 hours after purging with nitrogen gas.

Figure 6:
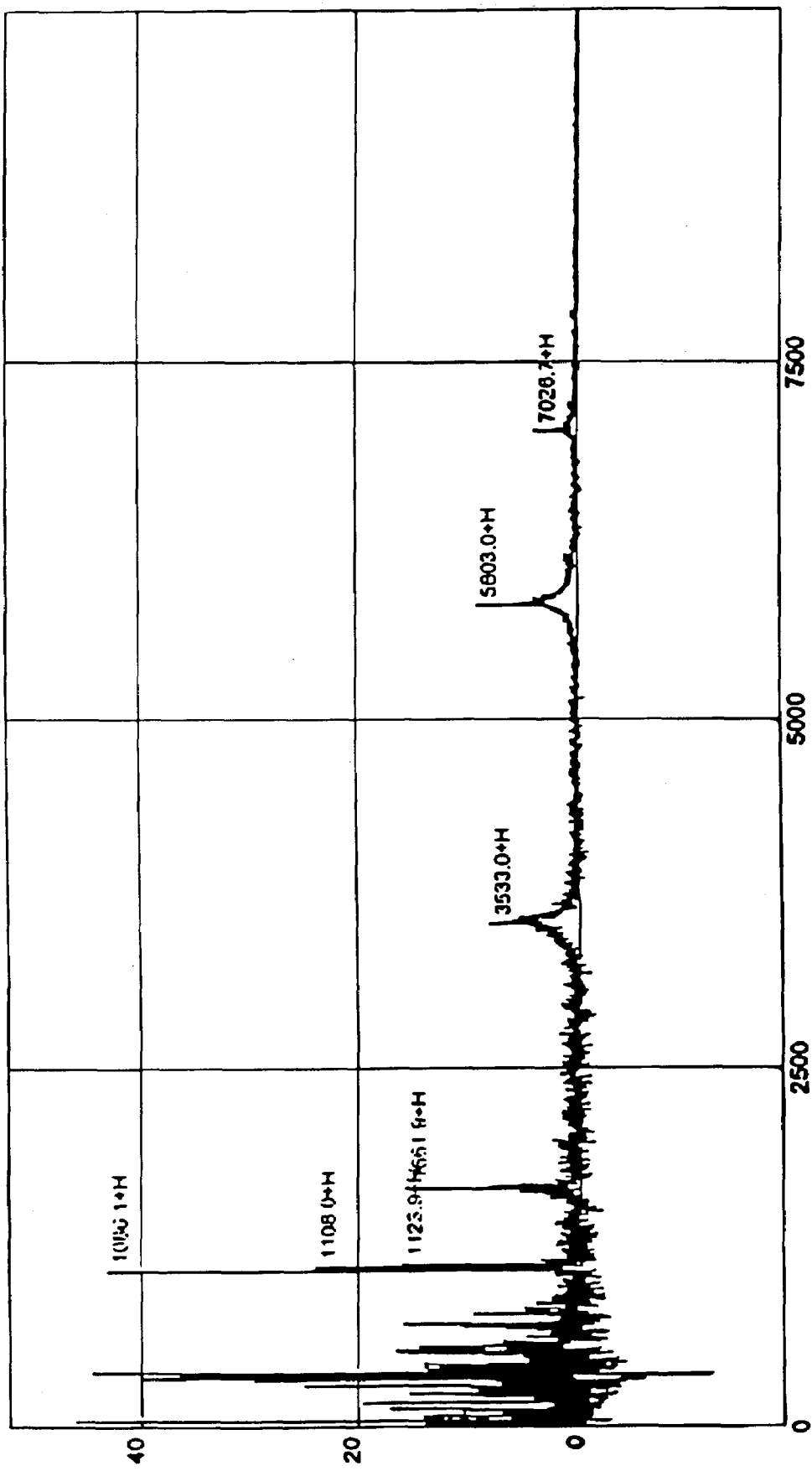
FIG. 6 is a mass spectrum of a peptide mixture, which was acquired using crosslinked CHCAMA on a gold chip.

The resulting polymer solution, 1 µL, was placed on an 8 spot ProteinChip® array and the chip was dried in a vacuum oven at approximately 95° C. for up to 20 hours to remove the solvent. A peptide sample was applied to each spot and scanned on PBS II spectrometer in order to check the polymer's laser desorption/ionization (LDI) characteristics. The components of the peptide mixture were desorbed, ionized and resolved. The resulting mass spectrum is shown in FIG. 6.

Example 7

Synthesis of 4-methacryloyloxy-3-methoxycinnamic Acid

In a 100 mL three-necked glass reactor, 5.0 g of 4-hydroxy-3-methoxycinnamic acid (ferulic acid from Sigma-Aldrich, Milwaukee, Wis.; melting point: 168-171° C. recorded by IA6200) was added to a solution of 3.5 g of potassium hydroxide (Aldrich) in 60 g of water and 15 mL of acetone (from VWR) and the reactor was placed in an ice bath. Methacryloyl chloride (from Aldrich), 3.3 mL, was placed separately in a dropping funnel and was set onto the three-necked glass reactor. The methacryloyl chloride was added slowly drop-wise into the reactor. The reaction was continued in an ice bath for two hours.

The resulting reaction mixture was acidified with dilute aqueous hydrochloric acid. The precipitate was filtered off and dried in vacuo. The dried filter cake was dissolved in 12 mL of glacial acetic acid (from Aldrich) and cooled in a refrigerator overnight. The re-crystallized material was filtered, dried and dissolved in methanol (from Aldrich). The methanol solution was placed in a freezer overnight. The resulting crystals were filtered and dried in vacuo. The yield was 1.1 g: melting point 180-184° C.

Example 8

Polymerization of Linear α-cyano-4-methacryloyloxycinnamic Acid

In a small glass bottle, 3.2 mg of a-cyano-4-methacryloyloxycinnamic acid prepared according to the Example 1 was mixed with 100 µL of 1-butanol (from Aldrich) over a mildly heated water bath until the solution became clear. To the monomer solution, 1 µL of lauroyl peroxide 1-butanol solution (approximately 7% solution) was added and mixed well. The bottle was placed in an oven after purging with nitrogen gas and kept at 92° C. for 20 hours.

Figure 3:
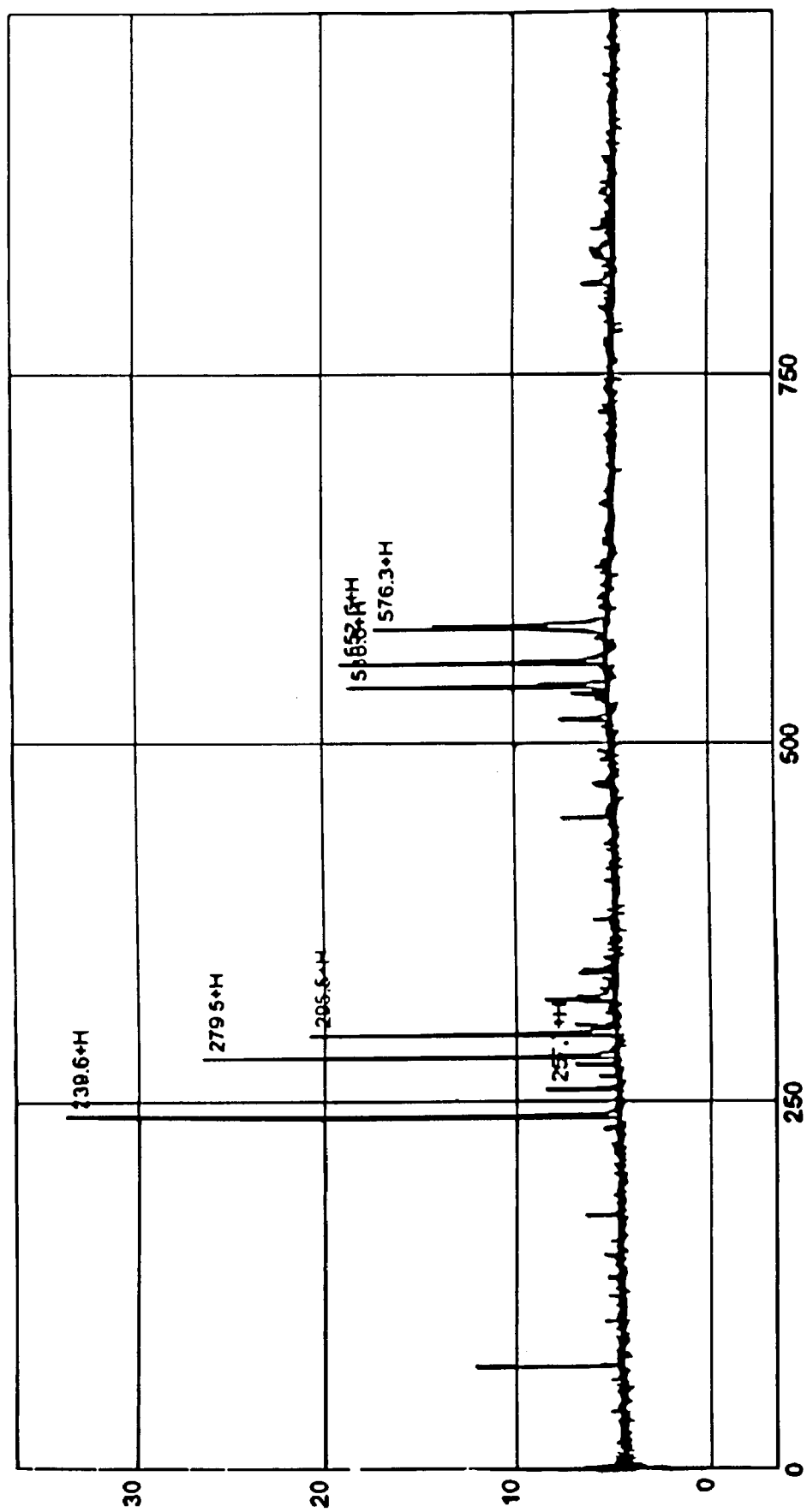
FIG. 3 is a mass spectrum of a peptide mixture, which was acquired using poly-CHCAMA on a gold chip.

The resulting polymer solution, 1 µL, was placed on an 8 spot ProteinChip® array and the chip was dried in a vacuum oven at approximately 95° C. for up to 20 hours to remove the solvent. A peptide sample was applied to each spot and scanned on PBS II spectrometer in order to check the polymer's laser desorption/ionization (LDI) characteristics. The components of the peptide mixture were desorbed, ionized and resolved. The resulting mass spectrum is shown in FIG. 3.

Example 9

Copolymerization of α-cyano-4-acryloyloxycinnamic Acid with Styrene

In a small glass bottle, 23.22 mg of a-cyano-4-acryloyloxycinnamic acid prepared according to the Example 2 was mixed with 1 mL of 1-butanol (from Aldrich) over a mildly heated water bath until the solution became clear. To the monomer solution, 20 μL of styrene monomer (from Aldrich) and 2 μL of lauroyl peroxide 1-butanol solution (approximately 7% solution) was added and mixed well. The bottle was placed in an oven after purging with nitrogen gas and kept at 92° C. for 20 hours. The resulting polymer solution, 1 μL, was placed on an 8 spot ProteinChip® array and the chip was dried in a vacuum oven at approximately 95° C. for up to 20 hours to remove the solvent. A peptide sample was applied to each spot and scanned on PBS II spectrometer in order to check the polymer's laser desorption/ionization (LDI) characteristics. The components of the peptide mixture were desorbed, ionized and resolved. The resulting mass spectrum is shown in FIG. 11.

Example 10

Copolymerization of 2,5-dimethacryloyoxy Benzoic Acid and Acrylic Acid

In a small glass bottle, 1.4 mg of 2,5-dimethacryloyoxy benzoic acid prepared according to the Example 3 was mixed with 50 μL of 1-hexanol (from Aldrich) over a mildly heated water bath until the solution became clear. To the monomer solution, 2 μL of acrylic acid (from Aldrich) 1 μL of lauroyl peroxide 1-hexanol solution (approximately 3% solution) was added and mixed well. The bottle was placed in an oven after purging with nitrogen gas and kept at 85° C. for 20 hours. The resulting polymer solution, 1 μL, was placed on an 8 spot ProteinChip® array and the chip was dried in a vacuum oven at approximately 95° C. for up to 20 hours to remove the solvent. A peptide sample was applied to each spot and scanned on PBS II spectrometer in order to check the polymer's laser desorption/ionization (LDI) characteristics. The components of the peptide mixture were desorbed, ionized and resolved. The resulting mass spectrum is shown in FIG. 12.

Example 11

Polymerization of 2,6-Dimethacryloyloxyacetophenone

Figure 13:
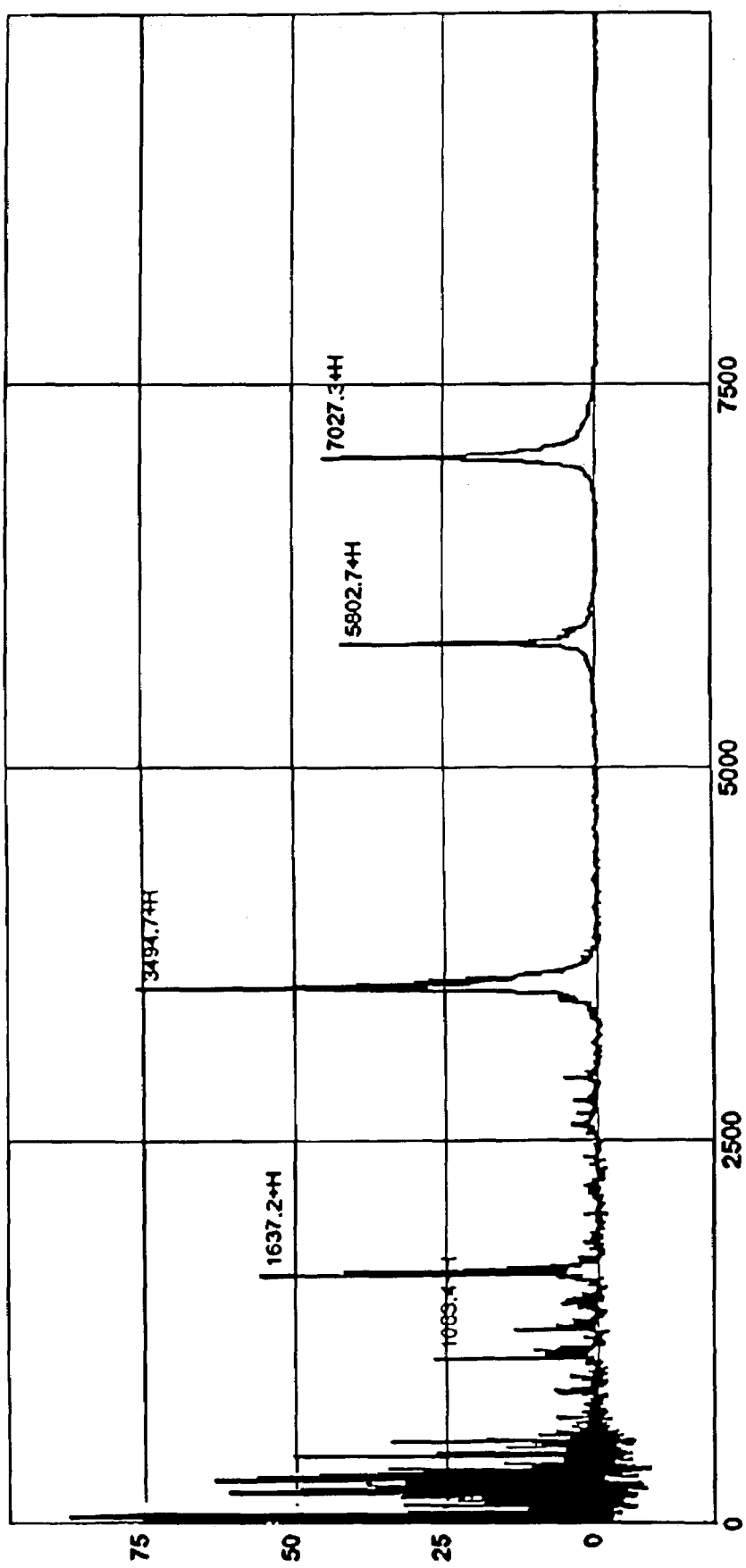
FIG. 13 is a mass spectrum of a peptide mixture, which was acquired using a polymer of 2,6-dimethacryloyloxyacetophenone.

In a small glass bottle, 1.76 mg of 2,6-Dimethacryloyloxyacetophenone prepared according to the Example 4 was mixed with 100 μL of 1-heptanol (from Aldrich) over a mildly heated water bath until the solution became clear. To the monomer solution, 1 μL of lauroyl peroxide 1-heptanol solution (approximately 3% solution) was added and mixed well. The bottle was placed in an oven after purging with nitrogen gas and kept at 95° C. for 20 hours. The resulting polymer solution, 1 μL, was placed on an 8 spot ProteinChip® array and the chip was dried in a vacuum oven at approximately 95° C. for up to 20 hours to remove the solvent. A peptide sample was applied to each spot and scanned on PBS II spectrometer in order to check the polymer's laser desorption/ionization (LDI) characteristics. The components of the peptide mixture were desorbed, ionized and resolved. The resulting mass spectrum is shown in FIG. 13.

Example 12

Copolymerization of α-cyano-4-methacryloyloxycinnamic Acid and Acrylic Acid.

Figure 14:
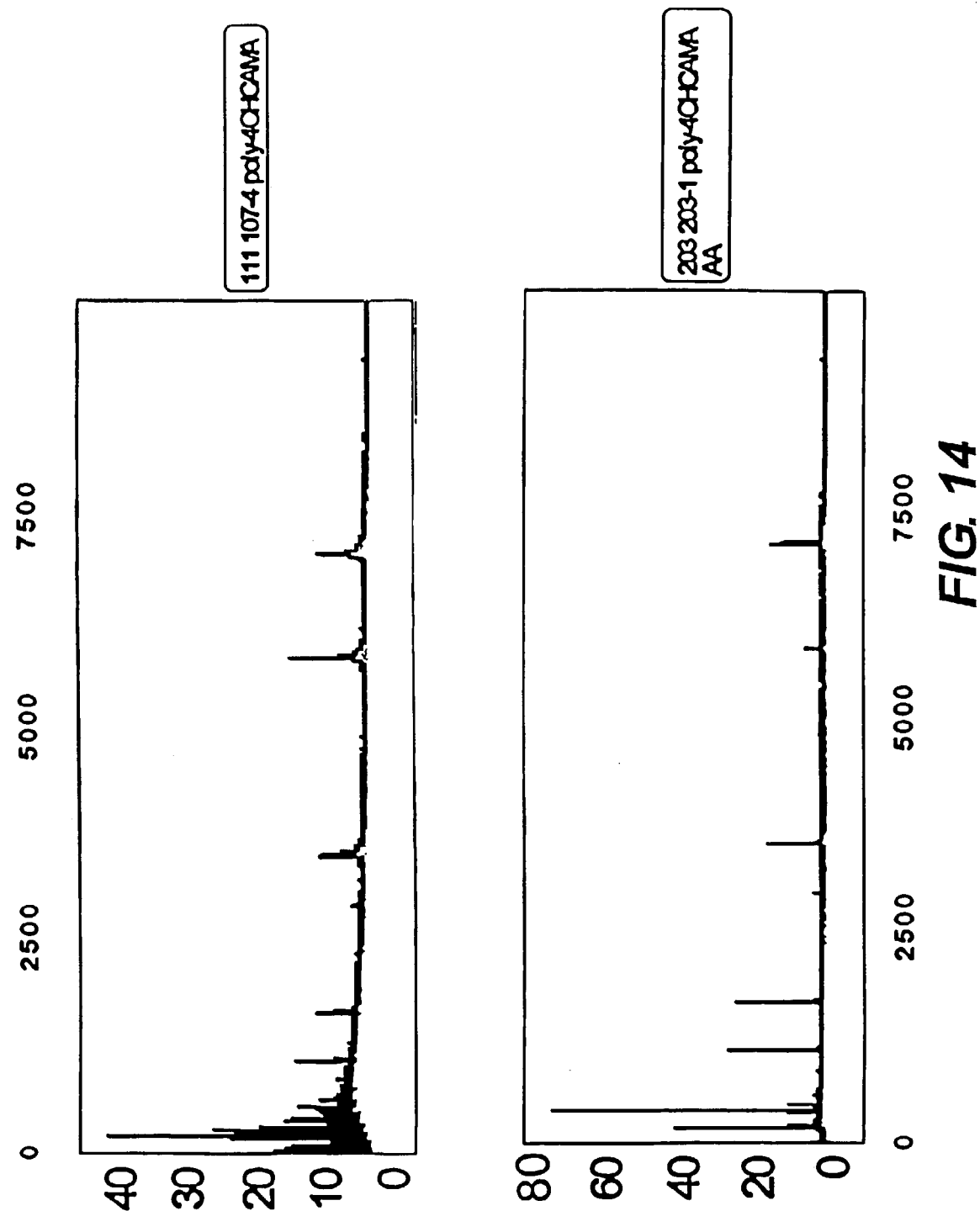
FIG. 14 are mass spectra of a peptide mixture, which were acquired using a co-polymer of α-cyano-4-methacryloxycinnamic acid and acrylic acid. The top figure shows desorption/ionization of peptide sample on laser irradiation using homopolymer with cyano-4-methacryloyloxycinnamic acid and the bottom figure shows desorption/ionization of peptide sample using a copolymer of cyano-4-methacryloyloxycinnamic acid and acrylic acid.

In a small glass bottle, 30.43 mg of α-cyano-4-methacryloyloxycinnamic acid (prepared according to the method in Example 1) and 20 μL of acrylic acid (Aldrich) were dissolved in 1 mL of 1-pentanol (Aldrich). To the above solution, 5 μL of 5% lauroyl peroxide (Aldrich) in 1-pentanol was added and mixed well. The small glass bottle with the monomer mixture was placed in an oven at 95° C. for 20 hours after purging with nitrogen gas. The resulting polymer solution, 1 μL, was placed on an 8 spot NP-20 ProteinChip® Array and the chip was dried in a vacuum oven at approximately 90° C. for 2 minutes to remove the solvent. A peptide sample was applied to each spot and scanned on PBS II spectrometer, in order to check the polymer's laser desorption/ionization (LDI) characteristics. The components of the peptide mixture were desorbed, ionized and resolved. Refer to FIG. 14. The top figure shows desorption/ionization of a peptide sample on laser irradiation using homopolymer of cyano-4-methacryloyloxycinnamic acid and the bottom figure shows desorption/ionization of a peptide sample using a copolymer of cyano-4-methacryloyloxycinnamic acid and acrylic acid.

Example 13

Copolymerization of α-cyano-4-acryloyloxycinnamic Acid with Acrylic Acid and 3-(trimethoxysilyl)-propyl Methacrylate In a small glass bottle, 26.45 mg of a-cyano-4-acryloyloxycinnamic acid (prepared according to the method in Example 2) was mixed with 1 mL of 1-pentanol (from Aldrich) over a mildly heated water bath, until the solution became clear. To the monomer solution, 40 μL of inhibitor-removed acrylic acid monomer (Aldrich), 20 μL of 3-(trimethoxysilyl)-propyl methacrylate (Aldrich) and 1 μL of lauroyl peroxide (5% solution in 1-pentanol) was added and mixed well. The bottle was placed in an oven after purging with nitrogen gas and kept at 92° C. for 20 hours. The resulting polymer solution, 1 μL, was placed on an 8 spot ProteinChip® array and the chip was dried in a vacuum oven at approximately 95° C. for up to 20 hours to remove the solvent. The resulting copolymer improved the adhesion to the glass substrate.

Example 14

Figure 15:
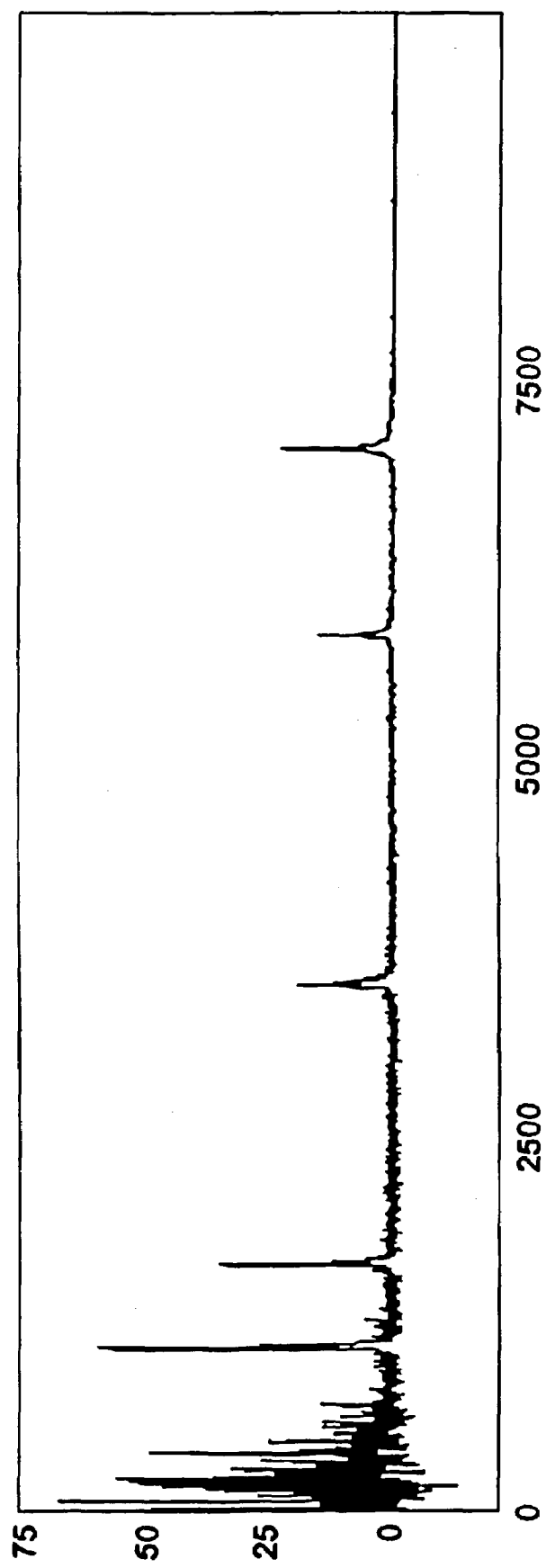
FIG. 15 is a mass spectrum of a peptide sample acquired using a co-polymer of α-cyano-4-methacryloyloxycinnamic acid and octadecylmethacrylate. The mass spectrum displays the spectra of peptides adsorbed on the polymer film of Example 13 using an ammonium sulfate solution.
Figure 16:
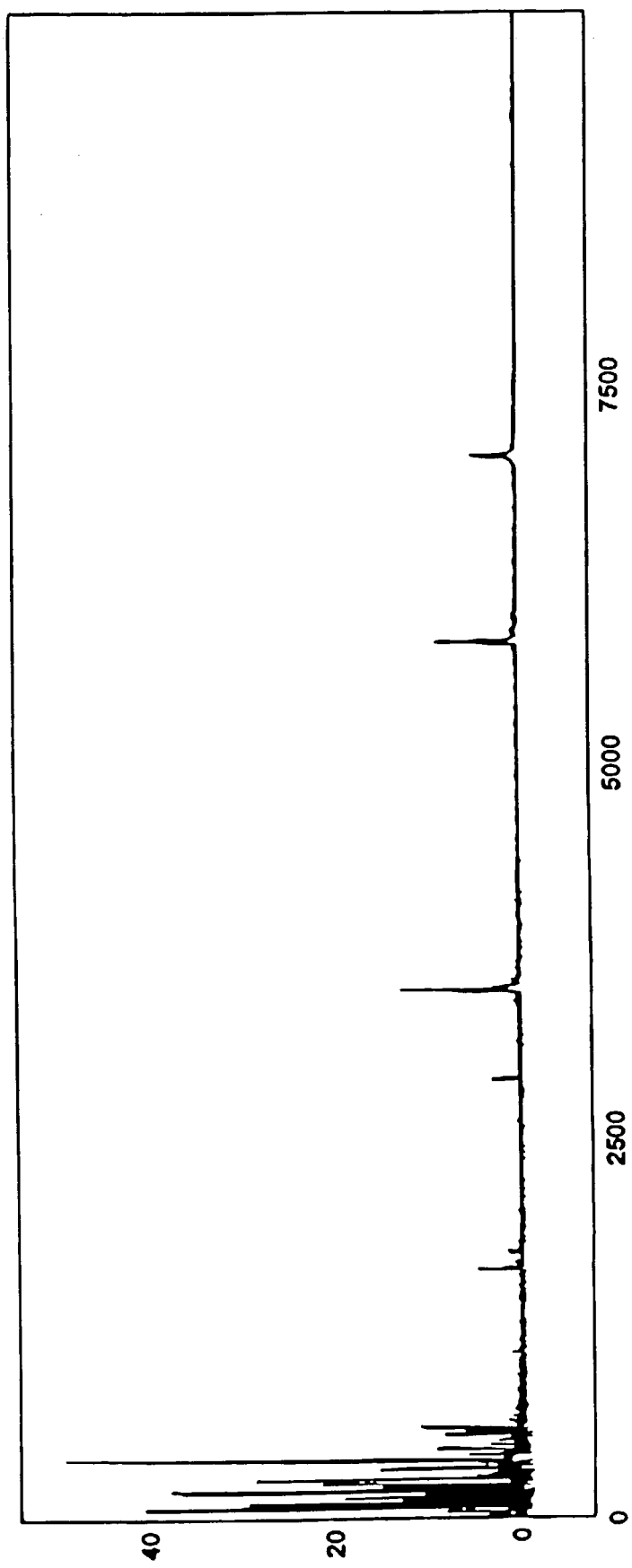
FIG. 16 is a mass spectrum of a peptide sample acquired using a co-polymer of α-cyano-4-methacryloyloxycinnamic acid and octadecylmethacrylate. The mass spectrum displays the spectra of peptides adsorbed on the polymer film of Example 13 using an urea solution.

Copolymerization of α-cyano-4-methacryloyloxycinnamic Acid, Octadecylmethacrylate In a small glass bottle, 8.20 mg of a-cyano-4-acryloyloxycinnamic acid (prepared according to the method in Example 2) was mixed with 200 μL of 1-pentanol (from Aldrich) over a mildly heated water bath until the solution became clear. To the monomer solution, 5 μL of n-octadecylmethacrylate monomer (Aldrich), 10 μL of 3-(trimethoxysilyl)-propyl methacrylate (Aldrich), and 1 μL of lauroyl peroxide (5% solution in 1-pentanol) was added and mixed well. The bottle was placed in an oven after purging with nitrogen gas and kept at 92° C. for 20 hours. The resulting polymer solution, 1 μL, was placed on an 8 spot ProteinChip® array and the chip was dried in a vacuum oven at approximately 90° C. for up to 20 hours to remove the solvent. A peptide sample was prepared using 1.7 M ammonium sulfate in 0.05 M sodium phosphate at pH of 7. The peptide sample (2 μL) was applied to each spot and the supernatant was removed by pipet tip. The cleaned chip was scanned on PBS II linear laser spectrometer in order to check the polymer's laser desorption/ionization (LDI) characteristics. The components of the peptide mixture, $Arg^8$-Vasopressin (1084.24 Daltons), Somatostatin (1637.90), Bovine Insulin β-chain (3495.94), Human Insulin (5807.65) and Hirudin BHVK (7033.61), were desorbed, ionized and resolved. The resulting spectrum is shown in the top figure. All five peptides were detected without the ammonium sulfate interference. A similar experiment was performed using peptides sample in urea solution. The five peptides sample was dissolved in 1 M urea solution and spotted spots on the same chip. After cleaning the chip surface by removing the supernatant, the chip was scanned on PBS II linear laser spectrometer in order to check the polymer's laser desorption/ionization (LDI) characteristics. The resulting spectrum is shown in the bottom figure. Peptides were detected without interference with urea. See, FIG. 15 and FIG. 16.

The results shows that bio-molecules in buffered and high concentrated salt can be applied directly to the polymer surface to selectively capture the bio-molecules to detect with LDI, without salt interference. The surface can selectively pick up target bio-molecules in a buffer, directly eliminating a cleaning step, e.g., salt removal, which demonstrates that the hydrophobic interaction chromatographic separation can be performed on the surface without further treatment of analyte solutions.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device comprising:
   (a) a metal substrate having a surface; and
   (b) a polymeric material attached to said surface, wherein said polymeric material comprises a photo-reactive polymer that absorbs photo-irradiation from a high fluence source to generate thermal energy, and transfers said thermal energy to allow desorption and ionization of an analyte in operative contact with said photo-reactive polymer, said photo-reactive polymer comprising a copolymer formed by copolymerization of octadecylmethacrylate and a polymerizable energy absorbing molecule, wherein said polymerizable energy absorbing molecule is a member selected from α-cyano-4-acryloyloxycinnamic acid; trans-3,5-dimethoxy-4-acryoyloxycinnamic acid;

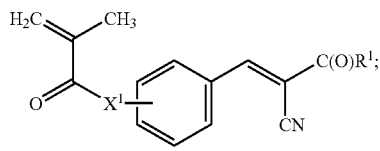

-continued

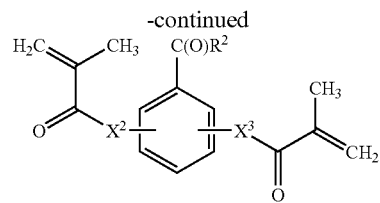

and combinations thereof,
   wherein
   $R^1$ is a member selected from the group consisting of H, $NR^4R^5$, $OR^6$, substituted or unsubstituted alkyl, substituted or unsubstituted heteroalkyl and substituted or unsubstituted aryl;
   $R^2$ is a member selected from the group consisting of $NR^4R^5$, $OR^6$, substituted or unsubstituted alkyl, substituted or unsubstituted heteroalkyl and substituted or unsubstituted aryl;
   $X^1$, $X^2$ and $X^3$, are members independently selected from the group consisting of O, and S; and
   $R^4$, $R^5$, $R^6$, $R^7$, and $R^8$ are members independently selected from the group consisting of H, substituted or unsubstituted alkyl, substituted or unsubstituted heteroalkyl and substituted or unsubstituted aryl.

2. The device according to claim 1, wherein said photo-reactive polymer comprises a copolymer formed by copolymerization of octadecylmethacrylate monomeric subunits and monomeric subunits having the formula

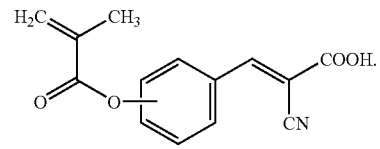

3. The device according to claim 1, wherein said photo-reactive polymer comprises a polymer formed by co-polymerization of octadecylmethacrylate, 3-(trimethoxysilyl)-propylmethacrylate spacer monomeric units, and

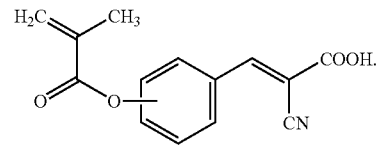

4. The device of claim 3 wherein the surface is coated with $SiO_2$.

5. The device of claim 4 wherein the polymeric material is covalently attached to the $SiO_2$ surface through silane moieties.

6. The device of claim 4 wherein the device is the device is in the form of a probe that is removably insertable into a mass spectrometer.

7. The device according to claim 1, wherein said polymeric material further comprises a binding functionality or a reactive functionality selected from an electrostatic functionality, a hydrophobic functionality, a hydrogen bonding functionality, a coordinate covalent bonding functionality, a covalent bonding functionality, an epoxide functionality, a carbonyldiimidazole functionality, a biospecific bonding functionality and combinations thereof.

8. The device according to claim 7, further comprising an analyte adsorbed onto said polymeric material through interaction with said binding functionality.

9. The device according to claim 7, wherein the photo-reactive polymer is a homo-polymer derivatized with the binding functionality.

10. The device according to claim 1, wherein the polymer is a linear polymer.

11. The device according to claim 10, wherein the linear polymer is a co-polymer.

12. The device according to claim 11, wherein the linear co-polymer comprises spacer monomeric subunits.

13. The device according to claim 11, wherein the linear co-polymer comprises monomeric units comprising a binding functionality or a reactive functionality selected from an electrostatic functionality, a hydrophobic functionality, a hydrogen bonding functionality, a coordinate covalent bonding functionality, a covalent bonding functionality, an epoxide functionality, a carbonyldiimidazole functionality, a biospecific bonding functionality and combinations thereof.

14. The device according to claim 1, wherein the photo-reactive polymer is a co-polymer comprising the photo-reactive monomeric subunits and functionalized monomeric subunits derivatized with a binding functionality or a reactive functionality selected from an electrostatic functionality, a hydrophobic functionality, a hydrogen bonding functionality, a coordinate covalent bonding functionality, a covalent bonding functionality, an epoxide functionality, a carbonyldiimidazole functionality, a biospecific bonding functionality and combinations thereof.

15. The device according to claim 1, wherein the polymeric material comprises a polymer blend comprising the photo-reactive polymer and a functionalized monomer or polymer derivatized with the binding functionality.

16. The device according to claim 1, wherein the polymer is a cross-linked polymer.

17. The device according to claim 16, wherein the cross-linked polymer further comprises spacer monomeric subunits.

18. The device according to claim 16, wherein the cross-linked polymer comprises monomeric units comprising a binding functionality or a reactive functionality selected from an electrostatic functionality, a hydrophobic functionality, a hydrogen bonding functionality, a coordinate covalent bonding functionality, a covalent bonding functionality, an epoxide functionality, a carbonyldiimidazole functionality, a biospecific bonding functionality and combinations thereof.

19. The device according to claim 1, wherein the polymeric material is attached to the surface by physical adhesion.

20. The device according to claim 1 or claim 3, wherein the surface comprises $SiO_2$ and the polymeric material is attached to the surface covalently.

21. The device according to claim 1, wherein the device is in the form of a probe that is removably insertable into a mass spectrometer.

22. The device according to claim 1, wherein the polymer is attached to the substrate in a plurality of addressable locations.

23. The device according to claim 1, wherein said polymerizable energy absorbing molecule is a member selected from

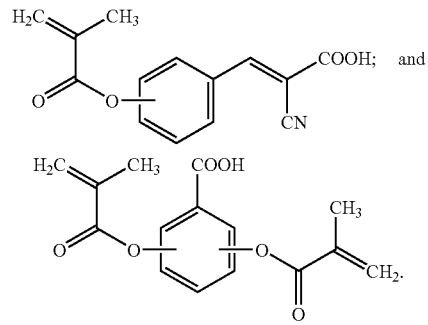

and combinations thereof,

24. A method of detecting an analyte comprising:
(a) contacting an analyte with a device, said device comprising:
  (i) a substrate having a surface; and
  (ii) a polymeric material attached to said surface, wherein said polymeric material comprises a photo-reactive polymer that absorbs photo-irradiation from a high fluence source to generate thermal energy, and transfers said thermal energy to allow desorption and ionization of an analyte in operative contact with said photo-reactive polymer, said polymer comprising monomeric subunits formed by polymerization of a polymerizable photo-reactive monomer;
(b) contacting an analyte with the polymeric material on the surface; and
(c) interrogating the surface of device with photo-irradiation from a high fluence source and detecting the analyte by gas phase ion spectrometry;
wherein said photo-reactive polymer comprises a copolymer formed by copolymerization of octadecyl-methacrylate and a polymerizable energy absorbing molecule, wherein said polymerizable energy absorbing molecule is a member selected from α-cyano-4-acryloyloxycinnamic acid; trans-3,5-dimethoxy-4-acryoyloxycinnamic acid;

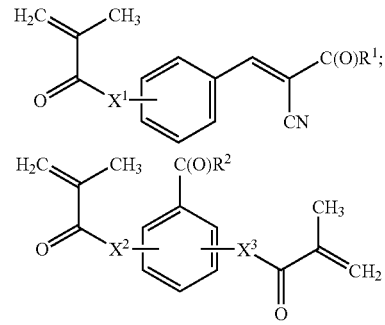

and combinations thereof,
wherein
$R^1$ is a member selected from the group consisting of H, $NR^4R^5$, $OR^6$, substituted or unsubstituted alkyl, substituted or unsubstituted heteroalkyl and substituted or unsubstituted aryl;

$R^2$ is a member selected from the group consisting of $NR^4R^5$, $OR^6$, substituted or unsubstituted alkyl, substituted or unsubstituted heteroalkyl and substituted or unsubstituted aryl;

$X^1$, $X^2$ and $X^3$, are members independently selected from the group consisting of O, and S; and $R^4$, $R^5$, $R^6$, $R^7$, and $R^8$ are members independently selected from the group consisting of H, substituted or unsubstituted alkyl, substituted or unsubstituted heteroalkyl and substituted or unsubstituted aryl.

25. The method of claim 24 wherein the gas phase ion spectrometry method is laser desorption/ionization mass spectrometry.

26. The method of claim 24 wherein the polymeric material comprises monomeric units comprising a binding functionality that captures the analyte.

* * * * *